(12) United States Patent  
Casey et al.

(10) Patent No.: US 6,670,342 B2
(45) Date of Patent: Dec. 30, 2003

(54) METHOD OF TREATING HEPATITIS DELTA VIRUS INFECTION

(75) Inventors: John L. Casey, Potomac, MD (US); Brent E. Korba, Laurel, MD (US); Paul J. Cote, New Market, MD (US); John L. Gerin, Bethesda, MD (US); Bud C. Tennant, Ithaca, NY (US); Chung K. Chu, Athens, GA (US)

(73) Assignees: Georgetown University, Washington, DC (US); Cornell Research Foundation, Inc., Ithaca, NY (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/821,278

(22) Filed: Mar. 29, 2001

(65) Prior Publication Data

US 2002/0160980 A1 Oct. 31, 2002

Related U.S. Application Data

(60) Provisional application No. 60/193,135, filed on Mar. 29, 2000.

(51) Int. Cl.[7] .................. C07D 405/04; A61K 31/7072; A61P 31/14

(52) U.S. Cl. .......................... 514/86; 514/88; 514/274; 544/309

(58) Field of Search ............................ 514/86, 88, 274; 544/309

(56) References Cited

U.S. PATENT DOCUMENTS 4,093,714 A 6/1978 Tolman et al.
4,210,638 A 7/1980 Greer (List continued on next page.)

FOREIGN PATENT DOCUMENTS

| EP | 0 350 287 | 1/1990 |
|---|---|---|
| EP | 0 650 371 | 11/2000 |
| WO | WO 89/02733 | 4/1989 |
| WO | WO 90/00555 | 1/1990 |
| WO | WO 91/16920 | 11/1991 |
| WO | WO 91/18914 | 12/1991 |
| WO | WO 91/19721 | 12/1991 |
| WO | WO 93/00910 | 1/1993 |
| WO | WO 94/26273 | 11/1994 |
| WO | WO 95/20595 | 8/1995 |
| WO | WO 96/15132 | 5/1996 |
| WO | WO 96/29336 A | 9/1996 |
| WO | WO 97/31641 A | 9/1997 |
| WO | WO 98/15375 | 4/1998 |

OTHER PUBLICATIONS

Fourel, et al; (1989) "Prolonged duck hepatitis B virus replication in duck hepatocytes cocultivated with rat epithelial cells: a useful system for antiviral testing"; *Hepatology* 10(2):186–191.

Fourel, et al; (1990) "Inhibitory effects of 2'–fluorinated arabinosyl–pyrimidine nucleosides on woodchuck hepatitis virus replication in chronically infected woodchucks"; *Antimicricrob Agents Chemother* Mar.; 34(3):473–5.

(List continued on next page.)

*Primary Examiner*—Mukund J. Shah
*Assistant Examiner*—Thomas McKenzie
(74) *Attorney, Agent, or Firm*—King & Spalding; Sherry M. Knowles; Joseph M. Bennett-Paris

(57) ABSTRACT

A method for the treatment for hepatitis delta infection in a host, that includes administering an effective amount of a nucleoside or a nucleoside analog that suppresses the expression of the hepatitis B surface or preS1 antigen in the host 100-fold or more relative to pretreatment values in vivo; or to not more than 1 microgram per milliliter in vivo. In a preferred embodiment, the nucleoside is L-FMAU, or a pharmaceutically acceptable salt or prodrug thereof.

16 Claims, 7 Drawing Sheets

L-FMAU

U.S. PATENT DOCUMENTS

| | | | |
|---|---|---|---|
| 4,211,771 A | 7/1980 | Witkowski et al. | |
| 4,382,925 A | 5/1983 | de Clercq et al. | |
| 4,468,384 A | 8/1984 | Bardos et al. | |
| 4,522,811 A | 6/1985 | Eppstein et al. | |
| 4,619,896 A | 10/1986 | Shattock et al. | |
| 4,666,892 A | 5/1987 | Fox et al. | |
| 5,149,794 A | 9/1992 | Yatvin et al. | |
| 5,194,654 A | 3/1993 | Hostetler et al. | |
| 5,223,263 A | 6/1993 | Hostetler et al. | |
| 5,246,924 A * | 9/1993 | Fox et al. | 514/49 |
| 5,256,641 A | 10/1993 | Yatvin et al. | |
| 5,411,947 A | 5/1995 | Hostetler et al. | |
| 5,463,092 A | 10/1995 | Hostetler et al. | |
| 5,486,520 A | 1/1996 | Belleau et al. | |
| 5,538,975 A | 7/1996 | Dionne | |
| 5,543,389 A | 8/1996 | Yatvin et al. | |
| 5,543,390 A | 8/1996 | Yatvin et al. | |
| 5,543,391 A | 8/1996 | Yatvin et al. | |
| 5,554,728 A | 9/1996 | Basava et al. | |
| 5,565,438 A | 10/1996 | Chu et al. | |
| 5,567,688 A | 10/1996 | Chu et al. | |
| 5,587,362 A | 12/1996 | Chu et al. | |
| 5,646,262 A | 7/1997 | Korba et al. | |
| 5,747,044 A | 5/1998 | Houghton et al. | |
| 5,750,350 A | 5/1998 | Houghton et al. | |
| 5,753,789 A | 5/1998 | Chu et al. | |
| 5,770,584 A | 6/1998 | Kucera et al. | |
| 5,808,040 A | 9/1998 | Chu et al. | |
| 5,932,219 A | 8/1999 | Houghton et al. | |
| 5,985,621 A | 11/1999 | Usman et al. | |
| 5,985,662 A | 11/1999 | Anderson et al. | |
| 6,020,167 A | 2/2000 | Thoma | |

OTHER PUBLICATIONS

Fourel, et al; (1992) "Effects of 2'–Fluorinated arabinosyl–pyrimidine nucleosides on duck hepatitis B virus DNA level in serum and liver of chronically infected ducks"; J Med Virol Jun.; 37(2):122–6.

Soike, et al; (1990) "Inhibition of simian varicella virus infection of monkeys by 1–(2–deoxy–2–fluoro–1–beta–D–arabinofuranosyl)–5–ethyluracil(FEAU) and synergistic effects of combination with human recombinant interferon–beta"; Antiviral Res Apr.; 13(4):165–74.

Aguesse–Germon, S. et al. (1998) Antimicrob Agents Chemother 42, 369–76.

Chu, C. et al. (1998) in Therapies for viral hepatitis, eds. Schinazi, R. & Sommadossi, J, (International Medical Press, Atlanta), vol. pp 303–312.

Chu, C. K. et al. (1995) Antimicrob Agents Chemother 39, 979–81.

Cote, P. J. et al. 1993 Viral Immunology 6:161.169.

Davisson et al., J. Org. Chem., 52(9), 1794–1801 (1987).

Deepen, R. et al. "Assay of preS epitopes and preS1 antibody in hepatitis B virus carriers and immune persons" Med Microbiol Immunol (Berl). 1990;179(1):49–60.

Di Marco, V. et al. (1996) J. Viral Hepat 3, 123–8.

Doong, S. L. et al. (1991) Proc Natl Acad Sci U S A 88, 8495–9.

Farci, P. et al. (1994) N Engl J Med 330, 88–94.

Fu, L. et al. (1999) Biochem Pharmacol 57, 1351–9.

Hadziyannis, S. J. (1991) J Hepatol 13 Suppl 1:S21–6.

Ho, D.H.W. (1973) "Distribution of Kinase and deaminase of 1β–D–arabinofuranosylcytosine in tissues of man and mouse." Cancer Res. 33, 2816–2820.

Hoard et al., (1965) J. Am. Chem. Soc., 87(8), 1785–1788.

Holy, A., et al., Synthetic Procedures in Nucleic Acid Chemistry, V1, 163–67.

Hong, C.I. et al. (1979a) "Synthesis and antitumor activity of 1β–D–arabino–furanosylcytosine conjugates of cortisol and cortisone." Biochem. Biophys. Rs. Commun. 88, 1223–1229.

Hong, C.I., et al. (1985) Nucleoside conjugates. 6. Synthesis and comparison of antitumor activity of 1–(β–D–arabinofuranosyl) cytosine conjugates of corticosteriods and selected lipophilic alcohols. J. Med. Chem. 28, 171–177.

Hoofnagle, J. et al. (1987) Prog Clin Biol Res 234, 291–8.

Hostetler, K.Y. et al. (1992) "Greatly enhanced inhibition of human immunodeficiency virus type 1 replication in CEM and HT4–6C cells by 3'–deoxythymidine diphosphate dimyristoylglycerol, a lipid prodrug of 3,–deoxythymidine." Antimicrob. Agents Chemother.36:2025.2029.

Hostetler, K.Y. et al. (1991); "Phosphatidylazidothymidine: mechanism of antiretroviral action in CEM cells." J. Biol Chem. 266, 11714–11717.

Hostetler, K.Y. et al. (1994a) "Antiviral activity of phosphatidyl–dideoxycytidine in hepatitis B–infected cells and enhanced hepatic uptake in mice." Antiviral Res. 24, 59–67.

Hostetler, K.Y., et al. (1994b) "Phosphatidylazidothymidine and phosphatidyl–ddC: Assessment of uptake in mouse lymphoid tissues and antiviral activities in human immunodeficiency virus–infected cells and in rauscher leukemia virus–infected mice." Antimicrobial Agents Chemother. 38, 2792–2797.

Hostetler, K.Y., et al. J. Biol. Chem. 265, 6112–6117.

Hunston, R.N. et al. (1984) "Synthesis and biological properties of some cyclic phosphotriesters derived from 2'–deoxy–5–fluorouridine." J. Med. Chem. 27, 440–444.

Imai et al., J. Org. Chem., 34(6), 1547–1550 (Jun. 1969).

Ji, Y.H., et al. (1990); "Monophosphoric acid esters of 7–β–hydroxycholesterol and of pyrimidine nucleoside as potential antitumor agents: synthesis and preliminary evaluation of antitumor activity." J. Med. Chem. 33 2264–2270.

Jones, A.S., et al. (1984) "Synthesis, properties, and biological activity of some nucleoside cyclic phosphoramidates." J. Chem. Soc. Perkin Trans. I, 1471–1474.

Jones, R. et al. Antiviral Research, 27 (1995) 1–17.

Juodka, B.A. et al. (1974) "Synthesis of diribonucleoside phosph (P→N) amino acid derivatives." Coll. Czech. Chem. Comm. 39, 363–968.

Kataoka, S., et al. (1989) "Alkylated cAMP derivatives; selective synthesis and biological activities." Nucleic Acids Res. Sym. Ser. 21, 1–2.

Kataoka, S., et al. (1991) "A convenient synthesis of adenosine 3',5'–cyclic phosphate (cAMP) benzyl and methyl triesters." Heterocycles 32, 1351–1356.

Kinchington, D., et al. (1992) "Comparison of antiviral effects of zidovudine phosphoramidate and phosphorodiamidate derviatives against HIV and ULV in vitro." Antiviral Chem. Chemother. 3, 107–112.

Kodama, K., et al. (1989) "Antitumor activity and pharmacology of 1–β–D–arabinofuranosylcytosine–5'–stearylphosphate; an orally active derivative of 1–β–D arabinofuranosylcytosine." J. Cancer Res. 80, 679–685.

Korba Be et al. (1992) Antiviral Res. 19:55–70. HB611:.

Korba et al. Hepatology, (2000) 31, 1165–75.

Korba, B. et al. (1999) Antivir. Res. 41, A54.

Korth, M. et al. (1979) "The effects of adenosine– and guanosine 3',5' phosphoric and acid benzyl esters on guine-a–pig ventricular myocardium." *Naunyn–Schmiedeberg's Arch. Pharmacol.* 310, 103–111.

Kotra, L. P. et al. (1997)*J Med Chem* 40, 3635–44;.

Kucera, L.S., et al. (1990) "Novel membrane–interactive ether lipid analogs that inhibit infectious HIV–1 production and induce defective virus formation." *AIDS Res. Hum. Retro Viruses.* 6:491–501.

Kukhanova, M. et al. (1998) *Biochem Pharmacol* 55, 1181–7.

Kumar, A., et al. (1990) "Synthesis and biological evaluation of some cyclic phosphoramidate nucleoside derivatives." *J. Med. Chem*, 33, 2368–2375.

Lau, D. T. et al. (1999) *Hepatology* 30, 546–9.

Le Bec, C., et al. (1991) "Synthesis of lipophilic phosphate triester derivatives of 5–fluorouridine an arabinocytidine as anticancer prodrugs." *Tetrahedron Lett.* 32, 6553–6556.

Lichtenstein, J., et al. (1960) "The metabolism of exogenously supplied nucleotides by *Escherichia coli.*," *J. Biol. Chem.* 235(2), 457–465.

Luthy, J., et al. (1981) "Synthesis and toxicological properties of three naturally occurring cyanoepithioalkanes". *Mitt. Geg. Lebensmittelunters. Hyg.* 72, 131–133 (Chem. Abstr. 95, 127093).

Ma, T. et al. (1996) *J Med Chem* 39, 2835–43.

Ma, T. et al. (1996) *J Med Chem* 40, 2750–4.

McGuigan, C. et al. (1994) *Antiviral Chem. Chemother.* 5, 271–277.

McGuigan, C. et al. (1989) "Synthesis and biological evaluation of some phosphate triester derivatives of the anti–viral drug Ara." *Nucleic Acids Res.* 17, 6065–6075.

McGuigan, C., et al. (1990a) "Synthesis and evaluation of some novel phosphoramidate derivatives of 3' –azido–3' –deoxythymidine (AZT) as anti–HIV compounds." *Antiviral Chem. Chemother.* 1 107–113.

McGuigan, C., et al. (1990b) "Synthesis and anti–HIV activity of some novel substituted dialkyl phosphate derivatives of AZT and ddCyd." *Antiviral Chem. Chemother.* 1, 355–360.

McGuigan, C., et al. (1991) "Synthesis and anti–HIV activity of some haloalkyl phosphoramidate derivatives of 3'–azido–3' deoxythymidine (AZT); potent activity of the trichloroethyl methoxyalaninyl compound." *Antiviral Res.* 15, 255–263.

McGuigan, C., et al. (1993b) "Intracellular delivery of bioactive AZT nucleotides by aryl phosphate derivatives of AZT." *J. Med. Chem.* 36, 1048–1052.

Meyer, R. B., et al. (1973) "Synthesis of purine nucleoside 3', 5' –cyclic phosphoramidates." *Tetrahedron Lett.* 269–272.

Nagyvary, J. et al. (1973) "Studies on neutral esters of cyclic AMP," *Biochem. Biophys. Res. Commun.* 55, 1072–1077.

Namane, A.. et al. (1992) "Improved brain delivery of AZT using a glycosyl phosphotriester prodrug." *J. Med. Chem.* 35, 3039–3044.

Nargeot, J. et al. (1983) *Natl. Acad. Sci. U.S.A.* 80, 2395–2399.

Nelson, K.A. et al. (1987) "The question of chair–twist equilibria for the phosphate rings of nucleoside cyclic 3',5' monophosphates. $^1$HNMR and x–ray crystallographic study of the diastereomers of thymidine phenyl cyclic 3', 5'–monophosphate." *J. Am. Chem. Soc.* 109, 4058–4064.

Nerbonne, J.M., et al. (1984) "New photoactivatable cyclic nucleotides produce intracellular jumps in cyclic AMP and cyclic GMP concentrations." *Nature* 301, 74–46.

Netter, H. J. et al. (1993) *J Virol* 67, 3357–62.

Neumann, J.M., et al. (1989) "Synthesis and transmembrane transport studies by NMR of a glucosyl phospholipid of thymidine." *J. Am. Chem. Soc.* 111, 4270–4277.

Niro, G. A. et al. (1997) *Hepatology* 25, 728–734.

Ohno, R., et al. (1991) "Treatment of myelodysplastic syndromes with orally administered 1–β–D–arabinouranosylcytosine–5' stearylphosphate." *Oncology* 48, 451–455.

Pai, S. et al. (1996) *Antimicrob Agents Chemother* 40, 380–6.

Palomino, E., et al. (1989) "A dihydropyridine carrier system for sustained delivery of 2', 3' dideoxynucleosides to the brain." *J. Med. Chem.* 32, 22–625.

Peek, S. et al. (2001) *Hepatology* 33, 254–66.

Peek, S. F. et al. (1997) *Hepatology* 26, 425A(Abstract 1187).

Perkins, R.M., et al. (1993) "Activity of BRL47923 and its oral prodrug, SB203657A against a rauscher murine leukemia virus infection in mice." *Antiviral Res.* 20 (Suppl. I). 84.

Piantadosi, C., et al. (1991) "Synthesis and evaluation of novel ether lipid nucleoside conjugates for anti–HIV–1 activity." *J. Med. Chem.* 34, 1408–1414.

Pompon, A. et al. Decomposition pathways of the mono– and bis(pivaloyloxymethyl) esters of azidothymidine–5'–monophosphate in cell extract and in tissue culture medium. *Antiviral Chem. Chemother.* 5, 91–98.

Porres, J. C. et al. (1989) *J Hepatol* 9, 338–44.

Prisbe, E.J., et al. (1986) "Synthesis and antiherpes virus activity of phosphate an phosphonate derivatives of 9–[(1, 3–dihydroxy–2–propoxy)methyl] guanine." *J. Med. Chem.* 29, 671–675.

Puech, F., et al. (1993) "Intracellular delivery of nucleoside monophosphate through a reductase–mediated activation process." *Antiviral Res.* 22, 155–174.

Pugaeva, V.P., et al. (1969). "Toxicological assessment and health standard ratings for ethylene sulfide in the industrial atmosphere." *Gig. Trf. Prof. Zabol.* 14, 47–48 (*Chem. Abstr.* 72, 212).

Rizzetto, M., et al. (1983) *Ann Intern Med* 98, 437–41.

Rosina, F. et al. (1991) *Hepatology* 13, 1052–6.

Rosina, F.et al. (1987) *Prog Clin Biol Res* 234, 299–303.

Rosowsky, A., et al. (1982) "Lipophilic 5'–(alkylphosphate) esters of 1–β–D–arabinofuranosylcytosine and its $N^4$–acyl and 2.2'–anhydro–3'–O–acyl derivatives as potential prodrugs." *J. Med. Chem.* 25, 171–178.

Ross, W. (1961) "Increased sensitivity of the walker turnout towards aromatic nitrogen mustards carrying basic side chains following glucose pretreatment." *Biochem. Pharm.* 8, 235–240.

Ryu, E.K., et al. (1982). "Phospholipid–nucleoside conjugates. 3. Synthesis and preliminary biological evaluation of 1–β–D–arabinofuranosylcytosine 5' diphosphate [–], 2–diacylglycerols." *J. Med. Chem.* 25, 1322–1329.

Saffhill, R. et al. (1986) "The degradation of 5–iododeoxyuridine and 5–bromoethoxyuridine by serum from different sources and its consequences for the use of these compounds for incorporation into DNA." *Chem. Biol. Interact.* 57, 347–355.

Saneyoshi, M., et al. (1980) "Synthetic nucleosides and nucleotides. XVI. Synthesis and biological evaluations of a series of 1–β–D–arabinofuranosylcytosine 5'–alky or arylphosphates." *Chem. Pharm. Bull.* 28, 2915–2923.

Sastry, J.K. et al. (1992) "Membrane–permeable dideoxyuridine 5'–monophosphate analogue inhibits human immunodeficiency virus infection." *Mol. Pharmacol.* 41, 441–445.

Sells Ma, et al. (1988) *J. Virol.* 62:2836–2844.

Shakil, A. O. et al. (1997) *Virology* 234, 160–7.

Shuto, S. et al. (1988) *Pharm. Bull.* 36, 209–217.

Shuto, S., et al. (1987) "A facile one–step synthesis of 5' phosphatidiylnucleosides by an enzymatic two–phase reaction." *Tetrahedron Lett.* 28, 199–202.

Smedile, A. et al. (1986) *Hepatology* 6, 1297–302.

Smedile, A. et al. (1987) *Prog Clin Biol Res* 234, 235–41.

Smedile, A., et al. (1992) *Int J Clin Lab Res* 22, 211–215.

Smedile, A., et al. (1994) *Prog Liver Dis* 12, 157–75.

Stein et al., Phosphorothioate Oligodeoxy–Nucleotide Analogues in "Oligodeoxynucleotides—Antisense Inhibitors of Gene Expression" Cohen, Ed. McMillan Press, London (1988).

Sureau, et al., Production of Infectious Hepatitis Delta Virus In Vitro and Neutralization with Antibodies Directed against Hepatitus B Virus Pre–S Antigens, *Journal of Virology*, Feb. 1992, p 1241–1245.

Tann, C.H. et al. (1985) *J. Org. Chem.* 50, 3644–47.

Thomas, H. C. et al. (1987) *Prog Clin Biol Res* 234, 277–90.

Ueda K, et al. (1989) *Virology* 169:213–216.

Vargha, L. *Chem. Ber.*, 1954, 87, 1351.

Witcher, J. W. et al. (1997) *Antimicrob Agents Chemother* 41, 2184–7).

Wright, J. D. et al. (1995) *Liver Transplant Surgery* 1, 30–42.

Wright, J. D. et al. (1995) *Pharm Res* 12, 1350–3.

Wright, J.D. et al. (1996) *Biopharm Drug Dispos* 17, 197–207.

Xu, A. S. et al. (1998) *Biochem Pharmacol* 55, 1611–9.

Yao, G. Q. et al. (1996) *Biochem Pharmacol* 51, 941–7).

Zhu, Y. et al. (2001) *J. Virol* 75, 311–22.

Schinazi, R.F. and Sommadossi, J–P., *Antiviral Therapy*, 3(3), pp. vii–ix, 1998.

* cited by examiner

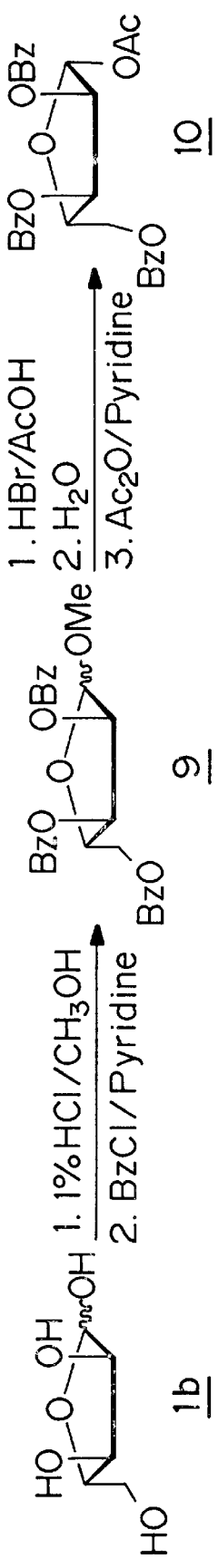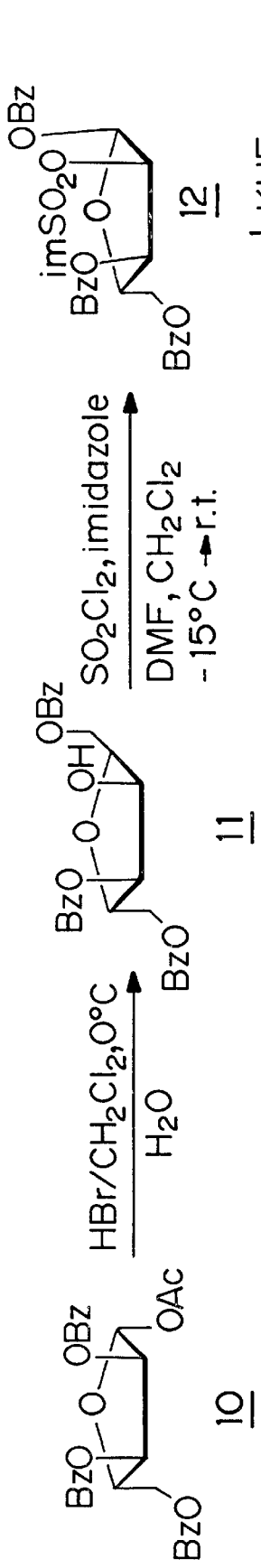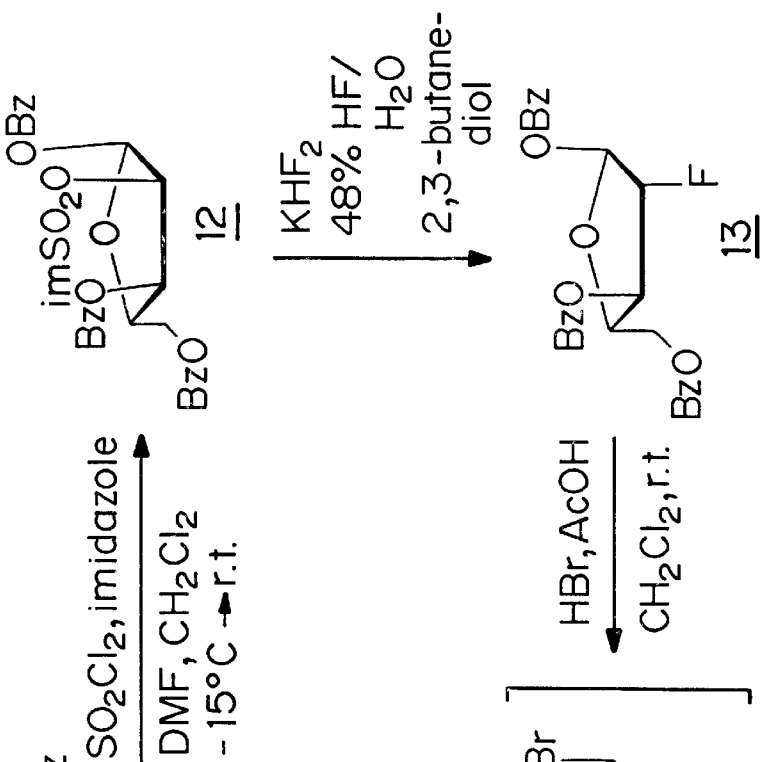
FIG. 3
FIG. 4

◆ 4553    ✱ 4857
△ 4559    ■ 4562
● 4856

● — 4553
△ — 4559
● — 4856
✱ — 4857
■ — 4562

METHOD OF TREATING HEPATITIS DELTA VIRUS INFECTION

This application claims priority to U.S. Ser. No. 60/193,135, filed on Mar. 29, 2000.

This invention was supported in part by the United States Department of Health and Human Services under grant numbers NIH AI-35164, AI-33655, AI-05399, N01-AI-45197 and N01-AI-82698.

FIELD OF INVENTION

This invention is in the area of methods and compositions for the treatment of a host infected with hepatitis delta virus (also referred to as "HDV") that includes administering an effective amount of a compound, in particular a nucleoside or nucleoside analog, that substantially reduces the level of hepatitis B surface antigen. In one nonlimiting embodiment, the nucleoside analog is 2'-fluoro-5-methyl-β-L-arabinofuranosyl-uridine (also referred to as "L-FMAU") or a pharmaceutically acceptable salt or prodrug thereof.

BACKGROUND OF THE INVENTION

Type D hepatitis, the most severe form of viral hepatitis, is caused by infection with hepatitis D (delta) virus (HDV), a sub-viral satellite of hepatitis B virus (HBV) (Smedile, A., et al. (1994) *Prog Liver Dis* 12, 157–75). Compared with other agents of viral hepatitis, acute HDV infection is more often associated with fulminant hepatitis, a rapidly progressive, often fatal form of the disease in which massive amounts of the liver are destroyed. Chronic type D hepatitis is typically characterized by necroinflammatory lesions, similar to chronic HBV infection, but is more severe, and frequently progresses rapidly to cirrhosis and liver failure, accounting for the disproportionate association of chronic HDV infection with terminal liver disease (Smedile, A., et al. (1994) *Prog Liver Dis*12, 157–75; Rizzetto, M., et al. (1983) *Ann Intern Med* 98, 437–41). Although HDV infection affects fewer individuals than HBV alone, the resulting acute or chronic liver failure is a common indication for liver transplantation in Europe as well as North America (Smedile, A. & Rizzetto, M. (1992) *Int J Clin Lab Res* 22, 211–215; Wright, T. L. & Pereira, B. (1995) *Liver Transplant Surgery* 1, 30–42). Chronic disease affects 15 million persons worldwide, about 70,000 of whom are in the U.S. The Centers for Disease Control estimates 1,000 deaths annually in the U.S. due to HDV infection (Alter, M. J. & Hadler, S. C. (1993) *Prog Clin Biol Res* 382, 243–50; Alter, M. J. & Mast, E. E. (1994) *Gastroenterol Clin North Am* 23, 437–55).

There is currently no generally accepted effective therapy for type D hepatitis, and liver transplantation is the only option for the associated end-stage liver disease. Although interferon alpha has been moderately successful in treating some cases of type D hepatitis, the need for better treatment options is indicated by the very high doses required, variable responses, frequent relapse after cessation of treatment, and difficulties in drug administration (Thomas, H. C. et al. (1987) *Prog Clin Biol Res* 234, 277–90; Hoofnagle, J. et al. (1987) *Prog Clin Biol Res* 234, 291–8; Rosina, F. et al. (1987) *Prog Clin Biol Res* 234, 299–303; Rosina, F. et al. (1991) *Hepatology* 13, 1052–6; Farci, P. et al. (1994) *N Engl J Med* 330, 88–94; Hadziyannis, S. J. (1991) *J. Hepatol* 13 Suppl 1:S21–6; Di Marco, V. et al. (1996) *J Viral Hepat* 3, 123–8; Porres, J. C. et al. (1989) *J Hepatol* 9, 338–44).

Lamivudine (β-L-2',3'-dideoxy-3'-thiacytidine, 3TC) is a synthetic nucleoside shown to be effective in treating HIV and HBV infection. See U.S. Pat. No. 5,539,116 to Liotta et al. Lamivudine is known to cause sustained suppression of HBV replication during treatment (Nevens, F. et al. (1997) *Gastroenterology* 113:1258–1263). However, lamivudine does not improve disease activity or lower HDV-RNA levels in patients with chronic delta hepatitis (Lau, D. T.et al. (1999) *Hepatology* 30, 546–9). Lamivudine was recently approved in the U.S. and several other countries for treatment of chronic HBV infection. Prolonged treatment of chronic HBV carriers with lamivudine leads to decreased levels of HBV in serum and improved liver histology (Lai, C. L. et al. (1998) *N Engl J Med* 339, 61–8; Tyrrell, D. et al. (1993) *Hepatology* 18, 112A; Nevens, F. et al. (1997) *Gastroenterology* 113, 1258–63; Dienstag, J. L. et al. (1995) *N Engl J Med* 333, 1657–61). Despite the dramatic effects on HBV, lamivudine treatment of patients chronically infected with both HBV and HDV has little effect on circulating levels of HDV; more importantly, there is no improvement in disease activity even though HBV levels are suppressed (Honkoop, P. et al. (1997) *Hepatology* 24 (Suppl), 1219 (Abstract); Lau, D. T. et al. (1999) *Hepatology* 30, 546–9).

Additional forms of treatment have been tried. For example, suramin in vitro blocks the entry of the virion into hepatocytes, but it is too toxic to be acceptable for long term use in humans (Smedile, A., et al. (1994) *Prog Liver Dis* 12, 157–75). Acyclovir enhances HDV replication in vitro (Smedile, A., et al. (1994) *Prog Liver Dis* 12, 157–75). Ribavirin did not significantly affect virological or biochemical parameters and had severe side-effects (Smedile, A., et al. (1994) *Prog Liver Dis* 12, 157–75). Synthetic analogs of thymosin have also been ineffective in the treatment of HDV infection (Smedile, A. et al. (1994) *Prog Liver Dis* 12, 157–75).

None of the described treatments for HDV infection are generally accepted as effective. The HDV virion is composed of a ribonucleoprotein core and an envelope. The core contains HDV-RNA, and hepatitis delta antigen (HDAg), which is the only protein encoded by this virus (Wang, K. S. et al. (1986) *Nature* 323, 508–14). The envelope is formed by the surface antigen protein (hepatitis B surface antigen, or HBsAg) of the helper virus, hepatitis B. (Bonino, F. (1984) *Infect Immun* 43, 1000–5; Bonino, F. et al. (1981) *Hepatology* 1, 127–31; Bonino, F. et al. (1986) *J Virol* 58, 945–50). The envelope is the sole helper function provided by HBV. HDV is able to replicate its RNA within cells in the absence of HBV (Kuo, M. Y. et al. (1989) *J Virol* 63, 1945–50), but requires HBsAg for packaging and release of HDV virions (Wu, J. C. et al. (1991) *J Virol* 65, 1099–104; Ryu, W. S. et al. (1992) *J Virol* 66, 2310–2315.), as well as for infectivity (Sureau, C., et al. (1992) *J Virol* 66, 1241–5). As a result of the dependence of HDV on HBV, HDV infects individuals only in association with HBV.

Because the woodchuck hepatitis virus (WHV) is closely related to HBV (ca. 85% nucleic acid homology), it has been widely used as a model for HBV infection and disease in its natural host, the eastern woodchuck (*M. monax*) (Gerin, J. L. (1990) *Gastroenterol Jpn* 25 (Supp), 38–42; Tennant, B. C. et al. (1988) *Viral Hepatitis and Liver Disease*, 462–464). Experimentally infected woodchucks have also been used extensively for analysis and development of anti-HBV therapeutics. (Zahm, F. E. et al. (1998) *Ital J Gastroenterol Hepatol* 30, 510–6; Tennant, B. C. et al. (1998) *Hepatology* 28, 179–91; Mason, W. S. et al. (1998) *Virology* 245, 18–32; Korba, B. E. et al. (1996) *Hepatology* 23, 958–63; Hurwitz, S. et al. (1998) *Antimicrob Agents Chemother* 42, 2804–2809; Block, T. M. et al. (1998) *Nat Med* 4, 610–4; Cullen, J. M. et al. (1997) *Antimicrob Agents Chemother* 41, 2076–82; Fourel, G. et al. (1990) *Nature* 347, 294–8; Gangemi, J. et al. (1997) *Antivir Therap* 1, 64–70; Genovesi, E. V. et al. (1998) *Antimicrob Agents Chemother* 42, 3209–17; Korba, B. E. et al. (2000) *Antiviral Res* 45, 19–32; Korba, B. E. et al. (2000) *Antiviral Therapy* 55, 95–105; Korba, B. E. et al. (2000) *Antimicrobial Agents and Chemotherapy* 44, 19–32. The efficacy of several anti-HBV agents used to experimentally treat chronic WHV infection in woodchucks (araAMP, ribavirin, AZT, ACV, 3TC, famciclovir, FTC, alpha-interferon, fialuridine ganciclovir, thymosin alpha-1, combination therapy with 3TC and alpha-interferon or 3TC and famciclovir) has accurately paralleled the efficacy and toxicity profiles of these agents administered to HBV patients treated in the course of clinical trials. The similar efficacy observed in WHV infected woodchucks and HBV infected persons treated with anti-HBV agents demonstrates that the woodchuck animal model can be predictive for anti-HBV therapies in man (Zahm, F. E. et al. (1998) *Ital J Gastroenterol Hepatol* 30, 510–6; Tennant, B. C. et al. (1998) *Hepatology* 28, 179–91; Mason, W. S. et al. (1998) *Virology* 245, 18–32; Hurwitz, S. et al. (1998) *Antimicrob Agents Chemother* 42, 2804–09; Fourel, G. et al. (1990) *Nature* 347, 294–8; Gangemi, J. et al. (1997) *Antivir Therap* 1, 64–70; Genovesi, E. V. et al. (1998) *Antimicrob Agents Chemother* 42, 3209–17; Korba, B. E. et al. (2000) *Antiviral Res* 44, 19–32; Korba, B. E. et al. (2000) *Hepatology* 31, 1165–75; Korba, B. E. et al. (2000) *Antiviral Therapy* 5, 95–105; Korba, B. E. et al. (2000) *Antimicrob Agents Chemother* 44, 1757–60). Like HBV, WHV can support HDV particle formation and infection, and the eastern woodchuck has been a useful model for HDV infection (Negro, F. et al. (1989) *J Virol* 63, 1612–8; Parana, R., Gerard, F., Lesbordes, J. L., Pichoud, C., Vitvitski, L., Lyra, L. G. & Trepo, C. (1995) *J Hepatol* 22, 468–73; Ciccaglione, A. R. et al. (1993) *Arch Virol Suppl* 8, 15–21; Bergmann, K. F. et al. (1989) *J Immunol* 143, 3714–21; Ponzetto, A. et al. (1984) *Proc Natl Acad Sci USA* 81, 2208–12; Ponzetto, A. et al. (1987) *Prog Clin Biol Res* 234, 37–46).

The dependence of HDV on its helper virus, HBV, could suggest that successful treatment of HDV infection would follow successful treatment of the supporting HBV infection. Unfortunately, this does not appear to be the case, as illustrated by recent results obtained with the drug lamivudine (Glaxo-Wellcome, Inc.) (Honkoop, P. et al. (1997) *Hepatology* 24 (Suppl), 1219 (Abstract); Lau, D. T. et al. (1999) *Hepatology* 30, 546–9). The lack of an effect of lamivudine on disease in HBV-HDV infected patients underscores the direct role of HDV in disease severity in such patients. Although lamivudine inhibits HBV and WHV replication, it does not affect the production of viral surface antigen (Lau, D. T. et al. (1999) *Hepatology* 30, 546–9; Doong, S. L. et al. (1991) *Proc Natl Acad Sci USA* 88, 8495–9; Korba et al. *Hepatology*, (2000) 31, 1165–75). The life cycle of HBV and other representatives of this family of viruses (for example, WHV) is unique in that the process of replicating genomic copies of the virus and the production of viral proteins (for example, HBV or WHV surface antigens) are differentially regulated (Ganem, D. 1996. Hepadnaviridae; In "Fields Virology" Fields B N, Knipe D M, Howley P, ed. Lippincott-Raven, Philadelphia, p. 2703–2737). Therefore, antiviral agents, such as synthetic nucleosides (for example, lamivudine) which target viral polymerases, may significantly inhibit HBV replication (for example, as measured by a reduction in viremia), but not affect the level of viral MRNA or viral protein production (for example, as measured by the levels of HBV surface antigen in plasma or serum). Given that the life cycle of HBV is unique in differentially regulating viral proteins and that HBsAg can be produced from a number of alternative transcripts, it has not been known to date what parameters are essential to achieving a therapeutic end point for HDV.

U.S. Pat. No. 5,747,044 discloses recombinantly produced immunogenic HDV polypeptides useful as vaccines.

U.S. Pat. No. 5,932,219 to Chiron discloses the entire genome of the hepatitis D virus, a family of cDNA replicas of the entire HDV genome, and teaches that portions of these cDNA sequences are useful as probes to diagnose the presence of virus in clinical samples. The patent also discloses proteins encoded by the cDNA that are useful in the production of vaccines. In particular, the '219 patent discloses a vaccine for hepatitis D which incorporates the p24 and p27 viral polypeptides. U.S. Pat. No. 5,750,350 to Chiron claims a kit useful in the analysis of hepatitis D virus which includes a peptide encoded by ORF 5 of the HDV genome. U.S. Pat. No. 5,747,044 claims a recombinantly produced immunogenic particle which raises antibodies against HDV, wherein the particle includes an immunogenic polypeptide encoded within ORF 5 of the HDV nucleotide sequence or its complement.

U.S. Pat. No. 6,020,167 assigned to Medeva Holdings B. V. discloses a method for treating chronic hepatitis, and in particular, hepatitis B, that includes administering a composition containing antiHBsAg.

U.S. Pat. No. 5,770,584 discloses a method for treating hepatitis virus infection by administering alkyl lipids or alkyl lipid derivatives.

U.S. Pat. No. 4,619,896 discloses a process for unmasking delta antigen in the blood of an animal, that includes treating serum with a surfactant and optionally with an antibody-antigen dissociating agent. The blood derived delta antigen is used as a diagnostic agent in the detection and determination of different classes of antibodies to hepatitis D virus.

United States statutory invention registration H1,345 discloses a method for preventing or treating hepatitis virus by administering a protein-prenyl transferase inhibitor.

Sureau, et al., Production of Infectious Hepatitis Delta Virus In Vitro and Neutralization with Antibodies Directed against Hepatitis B Virus Pre-S Antigens, *Journal of Virology, February* 1992, p 1241–1245 discloses that HDV particles produced in vitro are infectious and that (i) infectious particles are coated with HBV envelope proteins that contain the pre-S1 and pre-S2 regions, (ii) epitopes of the pre-S1 and pre-S2 domains of HBV envelope proteins are exposed at the surface of HDV particles, and (iii) that antibodies directed against those epitopes have neutralizing activity against HDV.

The nucleoside analog L-FMAU [2'-fluoro-5-methyl-β-L-arabinofuranosyl-uridine] is a known compound and has been shown to have significant antiviral activity against HBV replication in cell culture, and against the related duck hepatitis B virus in both cell culture and infected ducks (Aguesse-Gennon, S. et al. (1998) *Antimicrob Agents Chemother* 42, 369–76; Balakrishna Pai, S. et al. (1996) *Antimicrob Agents Chemother* 40, 380–6; Chu, C. K. et al. (1995) *Antimicrob Agents Chemother* 39, 979–81; Fu, L. et al. (1999) *Biochem Pharmacol* 57, 1351–9; Kotra, L. P. et al. (1997) *J Med Chem* 40, 3635–44; Kukhanova, M. et al. (1998) *Biochem Pharmacol* 55, 1181–7; Ma, T. et al. (1997) *J Med Chem* 40, 2750–4; Ma, T. et al. (1996) *J Med Chem* 39, 2835–43; Xu, A. S. et al. (1998) *Biochem Pharmacol* 55, 1611–9; Yao, G. Q. et al. (1996) *Biochem Pharmacol* 51, 941–7); Peek, S. et al. (2001) *Hepatology* 33, 254–66; Zhu, Y. et al. (2001) *J. Virol* 75, 311–22.

U.S. Pat. Nos. 5,587,362 and WO 95/20595 to Chu et al. disclose and claim L-FMAU and its pharmaceutical compositions for the treatment of HBV, and provides a detailed description of the synthesis of the compound. U.S. Pat. No. 5,567,688 to Chu et al. claims a method for the treatment of HBV using L-nucleosides including L-FMAU. U.S. Pat. No. 5,565,438 to Chu et al., claims a method to treat humans infected with Epstein-Barr virus (EBV) with L-FMAU. U.S. Pat. Nos. 5,808,040 and 5,753,789 disclose the use of L-FMAU to stabilize an oligonucleotide by including the compound at the 5'-terminus, 3'-terminus, or the interior of the oligonucleotide. WO 98/15375 discloses a method for the manufacture of L-FMAU.

L-FMAU has been shown to be a remarkably potent and fast-acting antiviral agent against WHV replication in chronically-infected woodchucks (Korba, B. et al. (1999) Antivir. Res. 41, A54; Chu, C. et al. (1998) in *Therapies for viral hepatitis*, eds. Schinazi, R. & Sommadossi, J. (International Medical Press, Atlanta), Vol. pp 303–12; Peek, S. F. et al. (1997) Hepatology 26, 425A(Abstract 1187); Peek, S. F. et al. (2001) Hepatology 33, 254–66; Zhu, Y. et al. (2001) *J. Virol* 75, 311–22. It has also been disclosed that L-FMAU induces suppression of WHV surface antigen in serum (Korba, B. et al. (1999) *Antivir. Res.* 41, A54; Chu, C. et al. (1998) in *Therapies for viral hepatitis*, eds. Schinazi, R. & Sommadossi, J. (International Medical Press, Atlanta), Vol. pp 303–12; Peek, S. B. et al. (1997) *Hepatology* 26, 425A and Peek, S. B. et al. (2000) *Hepatology* 33, 254–66. L-FMAU has been shown to have a favorable pharmacokinetic profile and sufficient oral bioavailability in rats and woodchucks that make it suitable for once daily administration (Wright, J. D. et al. (1995) *Pharm Res* 12, 1350–3; Wright, J. D. et al. (1996) *Biopharm Drug Dispos* 17, 197–207; Witcher, J. W. et al. (1997) *Antimicrob Agents Chemother* 41, 2184–7).

Because of the large number of persons infected with hepatitis delta virus, the devastating effects of hepatitis delta virus infection on the individual, and the lack of effective treatments, there is a critical need for new and effective methods and compositions for the treatment of hepatitis delta virus infection.

Therefore, it is an object of the present invention to provide methods and compositions for the treatment of a host, including a human, infected with hepatitis delta virus.

It is a further object of the present invention to provide a method for identifying compounds effective in the treatment of hepatitis delta virus infection.

SUMMARY OF THE INVENTION

It has been now been discovered that administration of a nucleoside or nucleoside analog or a prodrug or a pharmaceutically acceptable salt thereof that substantially reduces the level of hepatitis B surface antigen (referred to herein as HBsAg) in a host is useful in the treatment of hepatitis delta viral infection in that host. By substantial reduction of HBsAg in a host it is meant that the nucleoside or nucleoside analog reduces the hepatitis B surface antigen at least approximately 100-fold or more, and preferably, 200- or 500-fold relative to pretreatment values in vivo or in vitro, or to not more than 1, and preferably, 0.5 or 0.1 microgram per milliliter in vivo, as measured in serum or plasma using any appropriate standard immunoassays for example the commercial assay for human HBsAg (AUSZYME™, Abbott Laboratories or that described for woodchuck hepatitis B surface antigen in: *Viral Immunology* 6:161.169; Cote, P. J., C. Roneker, K. Cass, F. Schodel, D. Peterson, B. Tennant, F. DeNoronha, and J. Gerin. 1993).

It was previously known that if a nucleoside or nucleoside analog does not significantly reduce the level of HBsAg in a hepatitis delta infected host, for example, 3TC (β-L-2',3'-dideoxy-3'-thiacytidine), then that nucleoside is not effective in the treatment of hepatitis delta virus. However, given that the life cycle of HBV is unique in differentially regulating viral proteins and that HBsAg can be produced from a number of alternative transcripts, it has not been known to date what parameters are essential to achieving a therapeutic end point for HDV, including whether reduction, as opposed to elimination, of HBsAg, by a nucleoside or nucleoside analog would translate into any therapeutic effect on HDV. Further, there previously existed no information on the degree of HBsAg suppression needed to achieve this desired outcome, as measured by serum concentrations or the length of treatment required for a sustained effect. Known nucleosides do not target all templates for HBsAg production and none are known to routinely suppress serum HBsAg levels. Finally, a host liver cell must be co-infected with both HBV or a hepadnavirus other than hepatitis B that supports HDV infection and hepatitis delta virus in order for HBsAg suppression to be effective against hepatitis delta virus formation, and the proportion of liver cells making HBsAg but not co-infected is not known in each case. Liver cells infected with HBV alone could contribute to the serum HBsAg levels, yet suppression of HBsAg in these cells would not impact on hepatitis delta virus formation.

It has now been established for the first time through the paradigm nucleoside, and a nonlimiting embodiment, L-FMAU, that if a nucleoside suppresses the production of HBsAg, so as to affect a substantial and sustained reduction in serum or plasma HBsAg levels, i.e., to approximately 100-fold or less than pretreatment values in vivo or in vitro, it will be useful in the treatment of hepatitis delta virus.

Therefore, in one aspect of the invention, a method for the treatment of HDV infected host, in particular a human, is provided that includes the administration of an effective amount of a nucleoside or nucleoside analog that reduces HBsAg in the infected host at least approximately 100-fold, and preferably 200- or 500- fold, or more relative to pretreatment values in vivo or in vitro; or to not more than approximately 1 microgram, or preferably 0.5 or 0.1 microgram, per milliliter, as measured in serum or plasma using standard immunoassays (such as the commercial assay for human HBsAg (AUSZYME™, Abbott Laboratories) or that described for woodchuck hepatitis B surface antigen in: *Viral Immunology* 6:161.169; Cote, P. J., C. Roneker, K. Cass, F. Schodel, D. Peterson, B. Tennant, F. DeNoronha, and J. Gerin. 1993.

In an alternative embodiment, it has been now been discovered that administration of a nucleoside or nucleoside analog that substantially reduces the level of preS1 antigen in a host is useful in the treatment of hepatitis delta viral infection in that host. By substantial reduction of preS1 antigen in a host it is meant that the nucleoside or nucleoside analog reduces the hepatitis B surface antigen at least approximately 100-fold or more, and preferably, 200- or 500-fold relative to pretreatment values in vivo or in vitro, using any appropriate assay, including that in: Deepen R, Heermann K H, Uy A, Thomssen R, Gerlich W H. "Assay of preS epitopes and preS1 antibody in hepatitis B virus carriers and immune persons" *Med Microbiol Immunol* (Berl). 1990;179(1):49–60.

In another aspect, a method for the treatment of an HDV infected host, in particular a human, is provided that includes the administration of an effective amount of an organic non-nucleoside small molecule (i.e., a molecule of molecular weight less than 500, which is other than a biologic material found in nature or a derivative or analog thereof retaining the desired activity, such as a peptide, protein, antibody, hormone, ribozyme, nucleic acid, or cytokine), and which is not a protein-prenyl transferase inhibitor or thymosin-alpha-1, that reduces HBsAg in the infected host to at least approximately 100-fold or more, and preferably at least 200- or 500-fold, relative to pretreatment values in vivo or in vitro; or to not more than 1 microgram, preferably 0.5 or 0.1 microgram per milliliter, as measured in serum or plasma using any appropriate assay, including standard immunoassays (such as the commercial assay for human HBsAg (AUSZYME™, Abbott Laboratories) or that described for woodchuck hepatitis B surface antigen in: *Viral Immunology* 6:161.169; Cote, P. J., C. Roneker, K. Cass, F. Schodel, D. Peterson, B. Tennant, F. DeNoronha, and J. Gerin. 1993.

In one embodiment, an effective amount of L-FMAU or a pharmaceutically acceptable salt or prodrug thereof is administered to a host in need thereof to treat a hepatitis delta viral infection. In a preferred embodiment L-FMAU is administered to a host in need thereof in the absence of its corresponding β-D enantiomer (i.e., in an enantiomerically enriched or enantiomerically pure form).

In another embodiment, L-FMAU is administered in combination with at least one other HBsAg or preS1 antigen lowering agent that can be another nucleoside, a nucleoside analog or a non-nucleoside for the treatment of a hepatitis delta infected host. In yet another embodiment, the hepatitis delta treating agent is administered in combination with a agent that has activity against hepatitis B, whether or not the anti-hepatitis B agent lowers the hepatitis B surface antigen.

In yet another embodiment, a method for treating hepatitis delta is provided that includes administering a compound, including a nucleoside, nucleoside analog or other small molecule as defined herein, that reduces the surface antigen of a hepadnavirus other than hepatitis B that supports HDV infection.

In another embodiment, a method for screening a compound, including a nucleoside or a nucleoside analog, that is effective in the treatment of HDV infection is provided that includes assessing whether the compound suppresses the expression of hepatitis B surface antigen 100-fold or more (and preferably 200- or 500-fold) relative to pretreatment values in vivo or in vitro; and preferably, to not more than 1 microgram (and preferably 0.5 or 0.1 microgram) per milliliter, as measured in serum or plasma using standard immunoassays (such as the commercial assay for human HBsAg (AUSZYME™, Abbott Laboratories) or that described for woodchuck hepatitis B surface antigen in: *Viral Immunology* 6:161.169; Cote, P. J., C. Roneker, K. Cass, F. Schodel, D. Peterson, B. Tennant, F. DeNoronha, and J. Gerin. 1993, using methods provided herein or otherwise available.

In another embodiment, a method for screening a compound, including a nucleoside or a nucleoside analog, that is effective in the treatment of HDV infection is provided that includes assessing whether the compound suppresses the expression of hepatitis B surface antigen 100-fold or more (and preferably 200- or 500-fold) relative to pretreatment values in vivo or in vitro; or to not more than 1 microgram (and preferably 0.5 or 0.1 microgram) per milliliter, as measured in serum or plasma using standard immunoassays (such as the commercial assay for human HBsAg (AUSZYME™, Abbott Laboratories) or that described for woodchuck hepatitis B surface antigen in: *Viral Immunology* 6:161.169; Cote, P. J., C. Roneker, K. Cass, F. Schodel, D. Peterson, B. Tennant, F. DeNoronha, and J. Gerin. 1993, using methods provided herein or otherwise available.

In another embodiment, a method for screening a compound, including a nucleoside or a nucleoside analog, that is effective in the treatment of HDV infection is provided that includes assessing whether the compound suppresses the expression of preS1 surface antigen 100-fold or more (and preferably 200- or 500-fold) relative to pretreatment values as measured in serum or plasma using standard immunoassays.

The invention is based on the fundamental discovery that L-FMAU, as the model active compound, suppresses the expression of hepatitis B surface antigen by a sufficient amount that it effectively inhibits the packaging and release of HDV virions. Evidence is presented herein that L-FMAU causes a substantial decrease in levels of HDV viremia by suppressing the expression of hepatitis B surface antigen.

In another embodiment, HDV infection can be treated in a host by administering at least one antisense oligonucleotide targeted to the RNA transcript of the hepatitis B surface antigen or preS1 antigen either alone or in combination with L-FMAU, or another HBsAg or preS1 antigen lowering nucleoside or nucleoside analog. The term "oligonucleotide" encompasses both oligomeric nucleic acid moieties of the type found in nature, such as the deoxyribonucleotide and ribonucleotide structures of DNA and RNA, and man-made analogues that are capable of binding to nucleic acids found in nature. The oligonucleotides of the present invention can be based upon ribonucleotide or deoxyribonucleotide monomers linked by phosphodiester bonds, or by analogues linked by methyl phosphonate, phosphorothioate, phosphoroamidate, phosphorodithioate, or other oligonucleotide stabilizing bonds. They may also comprise monomer moieties which have altered base structures or other modifications, but which still retain the ability to bind to naturally occurring DNA and RNA structures. Such oligonucleotides may be prepared by methods well-known in the art, for instance using commercially available machines and reagents available from Perkin-Elmer/Applied Biosystems (Foster City, Calif.).

It is preferred that an antisense oligonucleotide targeting the HBV surface antigen or preS1 gene sequence be chosen such that the oligonucleotide hybridizes within approximately 25 bases of the AUG start codon of the gene. Examples of antisense oligonucleotides directed to the HBV surface antigen and preS1 gene are described in U.S. Pat. No. 5,646,262 to Korba et al. and include (SEQ ID NO.: 1) CTTAGGACTACACTACAAGAG; (SEQ ID NO.: 2) GACTACACTACAAGAG; (SEQ ID NO.: 3) AGGACTACACTACAAGAGGTA; (SEQ ID NO.: 4) TACACTACAAGAGGTA; (SEQ ID NO.: 5) TCTTCCCCAGGATCCT; (SEQ ID NO.: 6) TTTGGGGCGGACATTG; (SEQ ID NO.: 7) CCTAAGAACAGTTGTT; (SEQ ID NO.: 8) GTACAAGTCGCGTCCCAGG; (SEQ ID NO.: 9) TAGGAGCTCTTCTAAC; (SEQ ID NO.: 10) TATTCCCTAGTCTTGT; (SEQ ID NO.: 11) CAAGAGGTACAAGTC; (SEQ ID NO.: 12) CGACCACCTTTCTAAGACGGG; (SEQ ID NO.: 13) CCTTTCTAAGACGGG; (SEQ ID NO.: 14) TAAGACGGGGTA; (SEQ ID NO.: 15) GACGGGGTACGACAT; (SEQ ID NO.: 16) GTACGACATCTAGAA. Other examples of antisense oligonucleotides for the treatment of HDV infection are disclosed in U.S. Pat. No. 5,985,662 to Isis Pharmaceuticals, Inc. and include: (SEQ ID NO.: 17) CCTGATGTGATGTTCTCCAT; (SEQ ID NO.: 18) GAACTGGAGCCACCAG- CAGG; (SEQ ID NO.: 19) GAAAGATTCGTCCCCATGC; and (SEQ ID NO.: 20) CCACTGCATGGCCTGAGGATG.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 3 is a schematic illustration of an alternative preparation of 1-O-acetyl-2,3,5-tri-O-benzoyl-β-L-ribofuranose (10).

FIG. 4 is a schematic illustration of a method for the preparation of 1,3,5-tri-O-benzoyl-2-deoxy-2-fluoro-β-L-arabinofuranose (13).

DETAILED DESCRIPTION OF THE INVENTION

Figure 1:
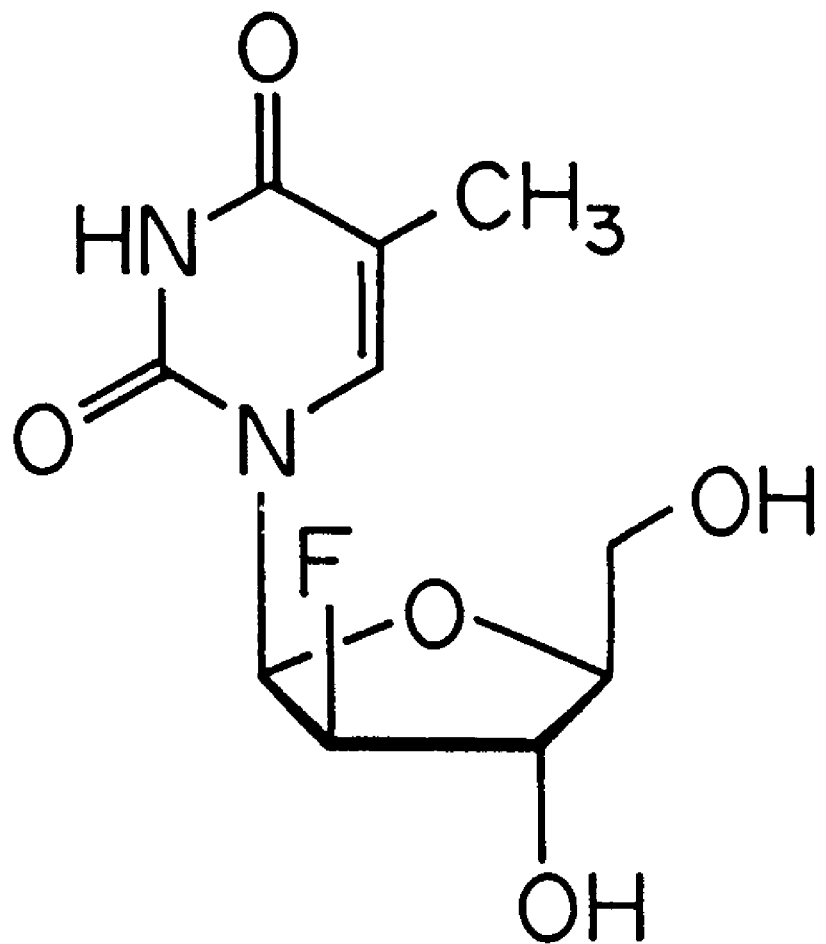
FIG. 1 is an illustration of L-FMAU (2'-fluoro-5-methyl-β-L-arabino-furanosyluridine).
Figure 2:
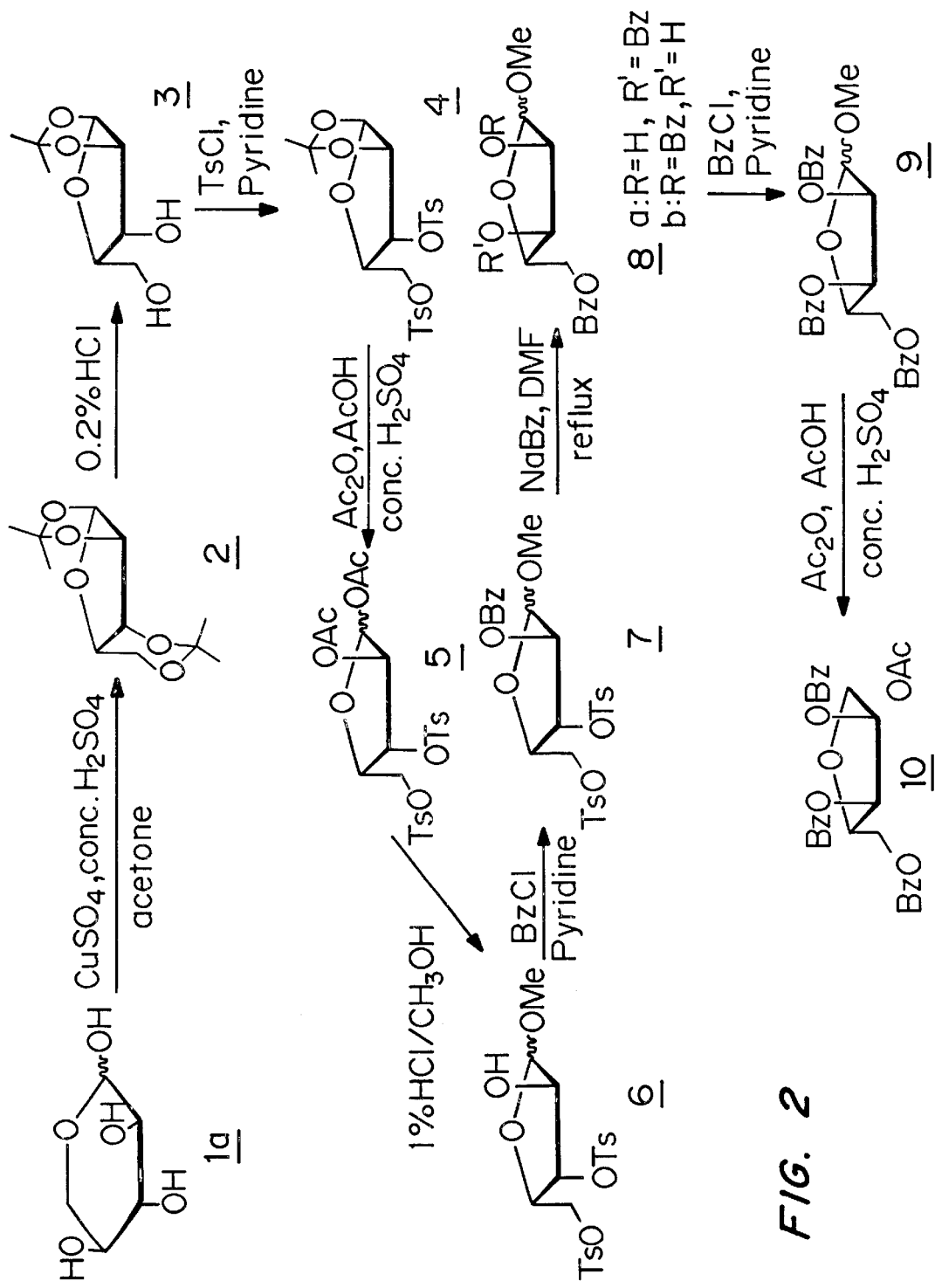
FIG. 2 is a schematic illustration of the preparation of 1-O-acetyl-2,3,5-tri-O-benzoyl-β-L-ribofuranose (10).
Figure 5:
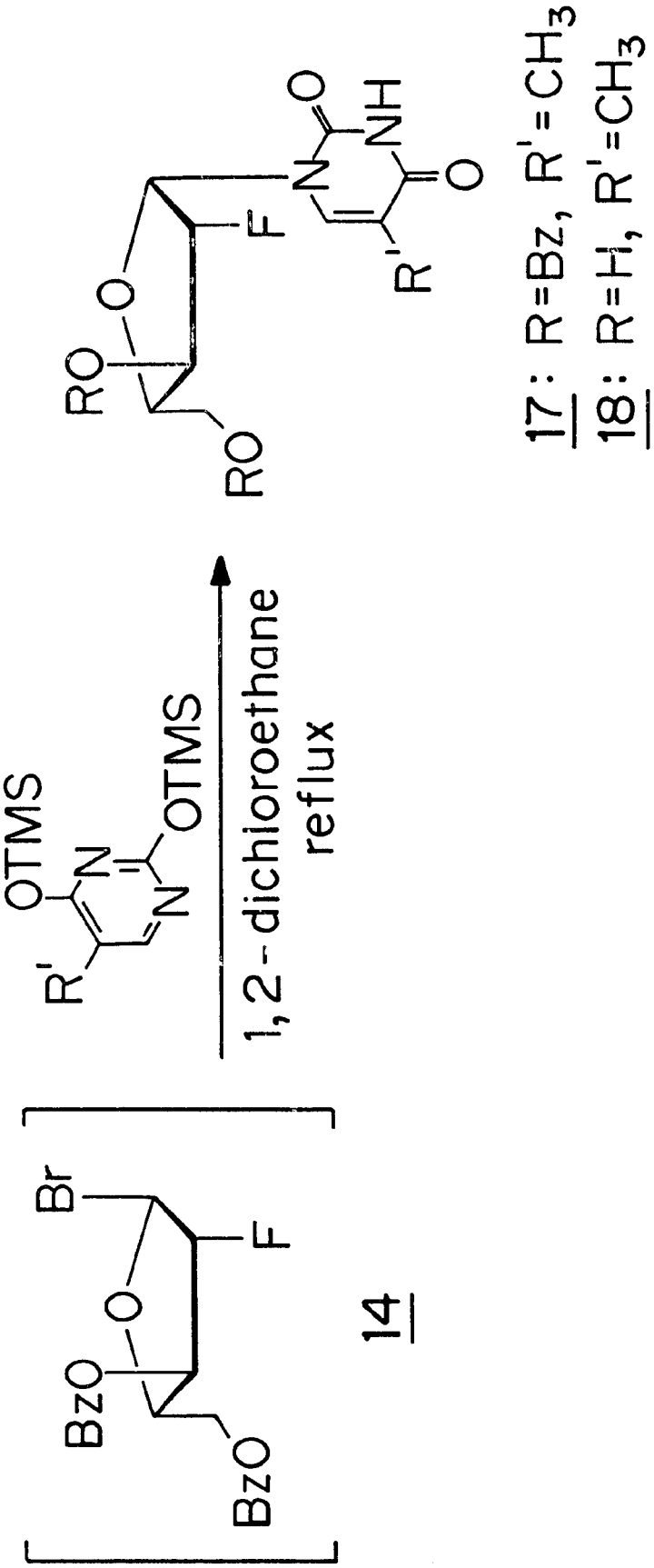
FIG. 5 is an illustration of a method for the preparation of 5'-benzoyl protected and unprotected 2'-deoxy-2'-fluoro-β-L-arabinofuranosyl]-5-methyl uridine (17 and 18).

The present invention is a method for the treatment of hepatitis delta virus (HDV) infection in a host, in particular a human, by administration of an effective amount of a nucleoside or nucleoside analog or a prodrug or a pharmaceutically acceptable salt thereof that provides a substantial and sustained reduction in the expression of hepatitis B surface antigen (HBsAg) or preS1 antigen. The unexpected failure of lamivudine, a compound known to suppress the replication of HBV, to lower HDV-RNA levels in patients demonstrates that the successful treatment of HBV does not necessarily correlate with a successful treatment of HDV. The present invention is based on the surprising discovery that compounds that provide a substantial and sustained reduction in the expression of hepatitis B surface antigen (HBsAg) or preS1 antigen, including L-FMAU, are potent inhibitors of HDV replication. L-FMAU is a particularly strong suppressor of hepatitis B surface antigen expression. This invention thus presents the fundamental discovery that the substantial and sustained suppression of the HBsAg or preS1 antigen can produce a significant reduction in HDV viremia in a host infected with these viruses. Alternatively, a host infected with hepatitis delta along with a hepadnavirus other than hepatitis B that supports HDV infection can be treated by substantially inhibiting the expression of surface antigen of that hepadnavirus.

In an embodiment of present invention, there is provided a method of treating a host infected with HDV, comprising the step of administering an effective amount of a nucleoside or nucleoside analog, or a pharmaceutical acceptable prodrug or salt thereof, optionally with pharmaceutically acceptable carrier, that substantially suppresses the expression of hepatitis B surface antigen or preS1 antigen.

In another embodiment of present invention, there is provided a method of treating a host infected with HDV, comprising the step of administering an effective amount of L-FMAU, or a pharmaceutical acceptable prodrug or salt, optionally in a pharmaceutically acceptable carrier.

In yet another embodiment, L-FMAU, or another nucleoside or nucleoside analog acting in like manner, or a pharmaceutical acceptable prodrug or salt thereof, optionally in pharmaceutically acceptable carrier, is administered to a host in need thereof, in combination with at least one other compound that reduces the level of hepatitis B surface antigen or preS1 antigen.

In still another embodiment of the present invention, there is provided a method of identifying a compound, including a nucleoside or nucleoside analog, that is effective in the treatment of HDV infection, comprising the steps of: a) administering a test compound to an animal model of hepatitis B virus, for example, the eastern woodchuck; b) monitoring the levels of hepatitis surface antigen or preS1 antigen, as appropriate, expressed in the animal treated with the test compound; c) comparing the levels of hepatitis surface antigen or preS1 antigen in animals treated with the test compound to control animals not treated with the test compound; d) selecting the compound in step (c) wherein the levels of hepatitis surface antigen or preS1 antigen are significantly lower that the levels of hepatitis surface antigen in animals not treated with the test compound, and in a preferred embodiment, 100-fold or more relative to pretreatment values in vivo or in vitro; or to not more than 1 microgram per milliliter, as measured in serum or plasma using standard immunoassays (such as the commercial assay for human HBsAg (AUSZYME™, Abbott Laboratories) or that described for woodchuck hepatitis B surface antigen in: *Viral Immunology* 6:161.169; Cote, P. J., C. Roneker, K. Cass, F. Schodel, D. Peterson, B. Tennant, F. DeNoronha, and J. Gerin. 1993.

In still another embodiment of the present invention, there is provided a method of identifying a compound, including a nucleoside or nucleoside analog, that is effective in the treatment of HDV infection, comprising the steps of: a) administering a test compound to a woodchuck chronically infected with woodchuck hepatitis virus and also infected with a woodchuck-adapted HDV inoculum; b) monitoring the levels of hepatitis surface antigen or preS1 antigen expressed in the animal treated with the test compound; c) comparing the levels of hepatitis surface antigen or preS1 antigen in animals treated with the test compound to control animals not treated with the test compound; d) selecting the compound in step (c) wherein the levels of hepatitis surface antigen or preS1 antigen are significantly lower than the levels of hepatitis surface antigen in animals not treated with the test compound, and in a preferred embodiment, 100-fold or more relative to pretreatment values in vivo or in vitro, or to not more than 1 microgram per milliliter, as measured in serum or plasma using standard immunoassays (such as the commercial assay for human HBsAg (AUSZYME™, Abbott Laboratories) or that described for woodchuck hepatitis B surface antigen in: *Viral Immunology* 6:161.169; Cote, P. J., C. Roneker, K. Cass, F. Schodel, D. Peterson, B. Tennant, F. DeNoronha, and J. Gerin. 1993.

In a preferred embodiment, a compound should be selected in which there is a concurrent reduction in the levels of hepatitis surface antigen or preS1 antigen and hepatitis D RNA in animals treated with the test compound.

In another embodiment of the present invention, there is provided a method of identifying a compound, including a nucleoside or nucleoside analog, that is effective in the treatment of HDV infection comprising the steps of: a) administering a test compound to an in vitro cell that has been transfected with human hepatitis B virus, such as 2.2.15 cells (see Sells M A, et al. (1988) *J. Virol.* 62:2836–2844. Korba B E and Gerin J L (1992) Antiviral Res. 19:55–70. HB611: Ueda K, et al. (1989) Virology 169:213–216); b) monitoring the levels of hepatitis surface antigen or preS1 antigen expressed in the animal treated with the test compound; c) comparing the levels of hepatitis surface antigen or preS1 antigen in the cells treated with the test compound to control animals not treated with the test compound; d) selecting the compound in step (c) wherein the levels of hepatitis surface antigen or preS1 antigen are significantly lower that the levels of hepatitis surface antigen in animals not treated with the test compound, and in a preferred embodiment, 100-fold, and preferably 200 or 500-fold or more relative to pretreatment values in vivo or in vitro.

In another embodiment of the present invention, there is provided a method of identifying a compound, including a nucleoside or nucleoside analog, that is effective in the treatment of HDV infection, comprising the steps of: a) administering a test compound to an in vitro cell that has been transfected to express both hepatitis B surface antigen or preS1 antigen and hepatitis delta virus (e.g. Casey, J. L., A. G. Polson, B. L. Bass, J. L. Gerin; p290–294: Viral Hepatitis and Liver Disease; M. Rizzetto et al., eds. Edizione Minerva Medica, Turin, 1997); b) monitoring the levels of hepatitis B surface antigen or preS1 antigen and hepatitis delta virus expressed intracellularly and secreted into the media of cells treated with the test compound; c) comparing the levels of hepatitis B surface antigen or preS1 antigen and hepatitis delta virus secreted from cells treated with the test compound to control cells not treated with the test compound; d) selecting the compound in step (c) wherein the secreted levels of hepatitis surface antigen or preS1 and hepatitis delta virus are significantly lower than the levels of hepatitis B surface antigen secreted from cells not treated with the compound.

I. Definitions

As used herein, the terms "HBsAg" and "hepatitis B surface antigen" refer to the surface antigen protein of any member of the hepadnavirus family, in particular including human hepatitis B virus (HBV) and woodchuck hepatitis virus (WHV).

As used herein, the term "enantiomerically pure" refers to a nucleoside composition that includes at least approximately 95%, and preferably approximately 97%, 98%, 99% or 100% of a single enantiomer of that nucleoside.

As used herein, the term "host" refers to any animal capable of infection with the hepatitis delta virus including but not limited to humans and other mammals.

The term "pharmaceutical salt" refers to a salt that retains the biological activity of the parent compound and does not impart undesired toxicological effects thereto. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art.

As used herein, the term "nucleoside" refers to heterocyclic nitrogenous base, preferably a purine or pyrimidine, in N-glycosidic or carbocyclic linkage with a carbohydrate or pseudo carbohydrate, preferably a pentose, or a sugar analog or a modified carbon ring system that can include one or more heteroatoms, and to which can be linked any desired substituent, and wherein the compound can be natural or synthetic, and wherein the nucleoside can exhibit any desired stereochemistry that achieves the desired result.

As used herein, the term "nucleoside analog" refers to a heterocyclic nitrogenous base, preferably a purine or pyrimidine, in N-glycosidic or carbocyclic linkage with an acyclic carbon chain that can include heteroatoms, and which can include substituents on the cyclic or acyclic chain, including a hydroxyl group.

The term "prodrug" is used throughout the specification to describe any derivative of the active compound, nucleoside or nucleoside analog that, upon administration to a patient, provides the parent active compound.

As used herein, the term purine or pyrimidine base, includes, but is not limited to, 6-alkylpurine and N6-alkylpurines, N6-acylpurines, N6-benzylpurine, 6-halopurine, N6-vinylpurine, N6-acetylenic purine, N6-acyl purine, N6-hydroxyalkyl purine, N6-thioalkyl purine, N2-alkylpurines, N4-alkylpyrimidines, N4-acyl-pyrimidines, 4-benzylpyrimidine, N4-halopyrimidines, N4-acetylenic pyrimidines, 4-acyl and N4-acyl pyrimidines, 4-hydroxyalkyl pyrimidines, 4-thioalkyl pyrimidines, thymine, cytosine, 6-azapyrimidine, including 6-azacytosine, 2- and/or 4-mercapto-pyrimidine, uracil, C5-alkylpyrimidines, C5-benzylpyrimidines, C5-halopyrimidines, C5-vinylpyrimidine, C5-acetylenic pyrimidine, C5-acyl pyrimidine, C5-hydroxyalkyl purine, C5-amidopyrimidine, C5-cyanopyrimidine, C5-nitropyrimidine, C5-amino-pyrimidine, N2-alkylpurines, N2-alkyl-6-thiopurines, 5-azacytidinyl, 5-aza-uracilyl, triazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl. Examples of bases include cytosine, 5-fluorocytosine, 5-bromocytosine, 5-iodocytosine, uracil, 5-fluorouracil, 5-bromo-uracil, 5-iodouracil, 5-methyluracil, thymine, adenine, guanine, inosine, xanthine, 2,6-diaminopurine, 6-aminopurine, 6-chloropurine and 2,6-dichloropurine, 6-bromo-purine, 2,6-dibromopurine, 6-iodopurine, 2,6-di-iodopurine, 5-bromovinylcytosine, 5-bromovinyluracil, 5-bromoethenylcytosine, 5-bromoethenyluracil, 5-trifluoromethyl-cytosine, 5-trifluoromethyluracil.

The term "protected" as used herein and unless otherwise defined refers to a group that is added to an oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

The term alkyl, as used herein, unless otherwise specified, refers to a saturated straight, branched, or cycline, primary, secondary, or tertiary hydrocarbon, typically of $C_1$ to $C_{18}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term lower alkyl, as used herein, and unless otherwise specified, refers to a $C_1$ to $C_4$ saturated straight or branched alkyl group.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo and fluoro.

As used herein, the term acyl refers to a moiety of the formula —C(O)R', wherein R' is alkyl; aryl, alkaryl, aralkyl, heterocyclic, alkoxyalkyl including methoxymethyl; arylalkyl including benzyl; aryloxyalkyl such as phenoxymethyl; aryl including phenyl optionally substituted with halogen, $C_1$ to $C_4$ alkyl or $C_1$ to $C_4$ alkoxy, or the residue of an amino acid.

The term amino acid includes naturally occurring and synthetic amino acids, and includes but is not limited to, alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, and histidinyl.

The term heterocyclic, as used herein, refers to a ringed moiety that includes at least one sulfur, oxygen, or nitrogen in the ring system. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxantinyl, and pteridinyl. Functional oxygen and nitrogen groups on the heterocyclic base can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl. The heterocyclic group can be substituted with any appropriate substituent, including but not limited to fluoro, iodo, bromo, chloro and lower alkyl, including cyclopropyl.

The term lipophilic prodrug refers to a nucleoside that contains a covalent substituent at the 5'-hydroxyl position that renders the nucleoside more lipophilic than the parent nucleoside with a 5'-hydroxyl group.

II. Active Compounds

It has been discovered that administration of any nucleoside, nucleoside analog, or certain non-nucleosides, as specified herein or a prodrug or pharmaceutically acceptable salt thereof that reduces the level of hepatitis B surface antigen (referred to herein as HBsAg) in a host to at least approximately 100-fold or more, and preferably, 200- or 500-fold relative to pretreatment values in vivo or in vitro; and preferably, to not more than 1, and preferably, 0.5 or 0.1 microgram per milliliter in vivo, is useful in the treatment of hepatitis delta viral infection in that host. The ability of a nucleoside to reduce the level of HBsAg to the required minimum level can be easily assessed by the methods described in detail herein, or other known methods.

It has been discovered that administration of any nucleoside, nucleoside analog, or certain non-nucleosides, or a prodrug or pharmaceutically acceptable salt thereof that reduces the level of preS1 antigen in a host to at least approximately 100-fold or more, and preferably, 200- or 500-fold relative to pretreatment values in vivo or in vitro. The ability of a nucleoside to reduce the level of preS1 antigen to the required minimum level can be easily assessed by known methods.

It was previously known that if a nucleoside or nucleoside analog does not significantly reduce the level of HBsAg in a hepatitis delta infected host, for example, 3TC (2',3'-dideoxy-3'-thiacytidine), then that nucleoside is not effective in the treatment of hepatitis delta virus. However, the converse had to date never been established, i.e., that if a nucleoside or nucleoside analog reduces the level of 100-fold or more relative to pretreatment values in vivo or in vitro, or to not more than 1 microgram per milliliter, as measured in serum or plasma using standard immunoassays (such as the commercial assay for human HBsAg (AUSZYME™, Abbott Laboratories) or that described for woodchuck hepatitis B surface antigen in: *Viral Immunology* 6:161.169; Cote, P. J., C. Roneker, K. Cass, F. Schodel, D. Peterson, B. Tennant, F. DeNoronha, and J. Gerin. 1993, it is useful in the treatment of hepatitis delta virus. This has now been established for the first time through the paradigm nucleoside analog, and a nonlimiting embodiment, L-FMAU.

III. Use of L-FMAU in the Treatment of HDV Infection

In one embodiment of the invention, an effective amount of a compound of Formula I, or a pharmaceutically acceptable prodrug or salt thereof, is administered of the structure:

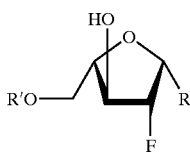

wherein R is 5-methyl uracil (also referred to as thymine) and R' is hydrogen, acyl, alkyl, monophosphate, diphosphate, triphosphate, or a stabilized phosphate derivative, including a 5'-ether lipid or a 5'-phospholipid, or a pharmaceutically acceptable salt thereof.

IV. Prodrugs of Active Compounds

The active compound can be administered as any derivative that upon administration to the recipient, is capable of providing directly or indirectly, the parent compound. Non-limiting examples are the pharmaceutically acceptable salts, and the 5' and purine or pyrimidine acylated or alkylated derivatives of the active compound (if a nucleoside or nucleoside analog). In one embodiment, the acyl group of the active compound is a carboxylic acid ester in which the non-carbonyl moiety of the ester group is selected from straight, branched, or cyclic alkyl, alkoxyalkyl including methoxymethyl, aralkyl including benzyl, aryloxyatkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g., dimethyl-t-butylsilyl) or diphenyl-methylsilyl. Aryl groups in the esters optimally comprise a phenyl group. The alkyl group can be straight, branched or cyclic, and is optimally a $C_1$ to $C_{18}$ group.

The active compound can be administered as a prodrug, including a nucleotide prodrug (if a nucleoside or nucleoside analog), to increase the activity, bioavailability, stability or otherwise alter the properties of the nucleoside. A "prodrug" is a therapeutic agent that is converted to an active form within the host by the action of endogenous enzymes or other chemicals and/or conditions. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect.

Examples of substituent groups that can replace one or more hydrogens on the phosphate moiety or hydroxyl are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides or other compounds to achieve a desire effect.

The active nucleoside or other hydroxyl containing compound can also be provided as an ether lipid (and particularly a 5'-ether lipid for a nucleoside), as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses*. 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythyrnidine diphosphate dimyristoylglycerol, a lipid prodrug of 3,-deoxythymidine." *Antimicrob. Agents Chemother.* 36:2025.2029; Hostetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside or other hydroxyl or amine containing compound, preferably at the 5'-OH position of the nucleoside or lipophilic preparations, include U.S. Pat. Nos. 5,149,794 (Sep. 22, 1992, Yatvin et al.); 5,194,654 (Mar. 16, 1993, Hostetler et al., 5,223,263 (June 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al.); and 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Nonlimiting examples of nucleotide prodrugs are described in the following references: Ho, D. H. W. (1973) "Distribution of Kinase and deaminase of 1β-D-arabinofuranosylcytosine in tissues of man and mouse." *Cancer Res.* 33, 2816–2820; Holy, A. (1993) Isopolar phosphorous-modified nucleotide analogues," In: De Clercq (Ed.), *Advances in Antiviral Drug Design*, Vol. I, JAI Press, pp. 179–231; Hong, C. I., Nechaev, A., and West, C. R. (1979a) "Synthesis and antitumor activity of 1β-D-arabino-furanosylcytosine conjugates of cortisol and cortisone."

Biochem. Biophys. Rs. Commun. 88, 1223–1229; Hong, C. I., Nechaev, A., Kirisits, A. J. Buchheit, D. J. and West, C. R. (1980) "Nucleoside conjugates as potential antitumor agents. 3. Synthesis and antitumor activity of 1-(β-D-arabinofuranosyl) cytosine conjugates of corticosteroids and selected lipophilic alcohols." *J. Med. Chem.* 28, 171–177; Hosteller, K. Y., Stuhmiller, L. M., Lenting, H. B. M. van den Bosch, H. and Richman *J. Biol. Chem.* 265, 6112–6117; Hosteller, K. Y., Carson, D. A. and Richman, D. D. (1991); "Phosphatidylazidothymidine: mechanism of antiretroviral action in CEM cells." *J. Biol Chem.* 266, 11714–11717; Hosteller, K. Y., Korba, B. Sridhar, C., Gardener, M. (1994a) "Antiviral activity of phosphatidyl-dideoxycytidine in hepatitis B-infected cells and enhanced hepatic uptake in mice." *Antiviral Res.* 24, 59–67; Hosteller, K. Y., Richman, D. D., Sridhar. C. N. Feigner, P. L. Feigner, J., Ricci, J., Gardener, M. F. Selleseth, D. W. and Ellis, M. N. (1994b) "Phosphatidylazidothymidine and phosphatidyl-ddC: Assessment of uptake in mouse lymphoid tissues and antiviral activities in human immunodeficiency virus-infected cells and in rauscher leukemia virus-infected mice." *Antimicrobial Agents Chemother.* 38, 2792–2797; Hunston, R. N., Jones, A. A. McGuigan, C., Walker, R. T., Balzarini, J., and DeClercq, E. (1984) "Synthesis and biological properties of some cyclic phosphotriesters derived from 2'-deoxy-5-fluorouridine." *J. Med. Chem.* 27, 440–444; Ji, Y. H., Moog, C., Schmitt, G., Bischoff, P. and Luu, B. (1990); "Monophosphoric acid esters of 7-β-hydroxycholesterol and of pyrimidine nucleoside as potential antitumor agents: synthesis and preliminary evaluation of antitumor activity." *J. Med. Chem.* 33 2264–2270; Jones, A. S., McGuigan, C., Walker, R. T., Balzarini, J. and DeClercq, E. (1984) "Synthesis, properties, and biological activity of some nucleoside cyclic phosphoramidates." *J. Chem. Soc. Perkin Trans.* I, 1471–1474; Juodka, B. A. and Smart, J. (1974) "Synthesis of diribonucleoside phosph (P→N) amino acid derivatives." *Coll. Czech. Chem. Comm.* 39, 363–968; Kataoka, S., Imai, J., Yamaji, N., Kato, M., Saito, M., Kawada, T. and Imai, S. (1989) "Alkylated cAMP derivatives; selective synthesis and biological activities." *Nucleic Acids Res. Sym. Ser.* 21, 1–2; Kataoka, S., Uchida, "(cAMP) benzyl and methyl triesters." *Heterocycles* 32, 1351–1356; Kinchington, D., Harvey, J. J., O'Connor, T. J., Jones, B. C. N. M., Devine, K. G., Taylor-Robinson D., Jeffries, D. J. and McGuigan, C. (1992) "Comparison of antiviral effects of zidovudine phosphoramidate and phosphorodiamidate derivatives against HIV and ULV in vitro." *Antiviral Chem. Chemother.* 3, 107–112; Kodaina, K., Morozumi, M., Saithoh, K. I., Kuninaka, H., Yosino, H. and Saneyoshi, M. (1989) "Antitumor activity and pharmacology of 1-β-D-arabinofuranosylcytosine-5'-stearylphosphate; an orally active derivative of 1-β-D-arabinofuranosylcytosine." *Jpn. J. Cancer Res.* 80, 679–685; Korty, M. and Engels, J. (1979) "The effects of adenosine- and guanosine 3',5' phosphoric and acid benzyl esters on guinea-pig ventricular myocardium." *Naunyn-Schmiedeberg's Arch. Pharmacol.* 310, 103–111; Kumar, A., Goe, P. L., Jones, A. S. Walker, R. T. Balzarini, J. and DeClercq, E. (1990) "Synthesis and biological evaluation of some cyclic phosphoramidate nucleoside derivatives." *J. Med. Chem*, 33, 2368–2375; LeBec, C., and Huynh-Dinh, T. (1991) "Synthesis of lipophilic phosphate triester derivatives of 5-fluorouridine an arabinocytidine as anticancer prodrugs." *Tetrahedron Lett.* 32, 6553–6556; Lichtenstein, J., Barner, H. D. and Cohen, S. S. (1960) "The metabolism of exogenously supplied nucleotides by *Escherichia coli.*," *J. Biol. Chem.* 235, 457–465; Lucthy, J., Von Daeniken, A., Friederich, J. Manthey, B., Zweifel, J., Schlatter, C. and Benn, M. H. (1981) "Synthesis and toxicological properties of three naturally occurring cyanoepithioalkanes". *Mitt. Geg. Lebensmittelunters. Hyg.* 72, 131–133 (*Chem. Abstr.* 95, 127093); McGigan, C. Tollerfield, S. M. and Riley, P.a. (1989) "Synthesis and biological evaluation of some phosphate triester derivatives of the anti-viral drug Ara." *Nucleic Acids Res.* 17, 6065–6075; McGuigan, C., Devine, K. G., O'Connor, T. J., Galpin, S. A., Jeffries, D. J. and Kinchington, D. (1990a) "Synthesis and evaluation of some novel phosphoramidate derivatives of 3'-azido-3'-deoxythymidine (AZT) as anti-HIV compounds." *Antiviral Chem. Chemother.* 1 107–113; McGuigan, C., O'Connor, T. J., Nicholls, S. R. Nickson, C. and Kinchington, D. (1990b) "Synthesis and anti-HIV activity of some novel substituted dialkyl phosphate derivatives of AZT and ddcyd." *Antiviral Chem. Chemother.* 1, 355–360; McGuigan, C., Nicholls, S. R., O'Connor, T. J., and Kinchington, D. (1990c) "Synthesis of some novel dialkyl phosphate derivative of 3'-modified nucleosides as potential anti-AIDS drugs." *Antiviral Chem. Chemother.* 1, 25–33; McGuigan, C., Devin, K. G., O'Connor, T. J., and Kinchington, D. (1991) "Synthesis and anti-HIV activity of some haloalkyl phosphoramidate derivatives of 3'-azido-3' deoxythymidine (AZT); potent activity of the trichloroethyl methoxyalaninyl compound." *Antiviral Res.* 15, 255–263; McGuigan, C., Pathirana, R. N., Balzarini, J. and DeClercq, E. (1993b) "Intracellular delivery of bioactive AZT nucleotides by aryl phosphate derivatives of AZT." *J. Med. Chem.* 36, 1048–1052.

Alkyl hydrogen phosphate derivatives of the anti-HIV agent AZT may be less toxic than the parent nucleoside analogue. *Antiviral Chem. Chemother.* 5, 271–277; Meyer, R. B., Jr., Shuman, D. A. and Robins, R. K. (1973) "Synthesis of purine nucleoside 3', 5'-cyclic phosphoramidates." *Tetrahedron Lett.* 269–272; Nagyvary, J. Gohil, R. N., Kirchner, C. R. and Stevens, J. D. (1973) "Studies on neutral esters of cyclic AMP," *Biochem. Biophys. Res. Commun.* 55, 1072–1077; Namane, A. Gouyette, C., Fillion, M. P., Fillion, G. and Huynh-Dinh, T. (1992) "Improved brain delivery of AZT using a glycosyl phosphotriester prodrug." *J. Med. Chem.* 35, 3039–3044; Nargeot, J. Nerbonne, J. M. Engels, J. and Leser, H. A. (1983) *Natl. Acad. Sci. U.S.A.* 80, 2395–2399; Nelson, K. A., Bentrude, W. G. Stser, W. N. and Hutchinson, J. P. (1987) "The question of chair-twist equilibria for the phosphate rings of nucleoside cyclic 3', 5' monophosphates. $^1$HNMR and x-ray crystallographic study of the diastereomers of thymidine phenyl cyclic 3', 5'-monophosphate." *J. Am. Chem. Soc.* 109, 4058–4064; Nerbonne, J. M., Richard, S., Nargeot, J. and Lester, H. A. (1984) "New photoactivatable cyclic nucleotides produce intracellular jumps in cyclic AMP and cyclic GMP concentrations." *Nature* 301, 74–76; Neumann, J. M., Herv_, M., Debouzy, J. C., Guerra, F. I., Gouyette, C., Dupraz, B. and Huyny-Dinh, T. (1989) "Synthesis and transmembrane transport studies by NMR of a glucosyl phospholipid of thymidine." *J. Am. Chem. Soc.* 111, 4270–4277; Ohno, R., Tatsumi, N., Hirano, M., Imai, K. Mizoguchi, H., Nakamura, T., Kosaka, M., Takatuski, K., Yamaya, T., Toyama K., Yoshida, T., Masaoka, T., Hashimoto, S., Ohshima, T., Kimura, I., Yamada, K. and Kimura, J. (1991) "Treatment of myelodysplastic syndromes with orally administered 1-β-D-arabinouranosylcytosine –5' stearylphosphate." *Oncology* 48, 451–455. Palomino, E., Kessle, D. and Horwitz, J. P. (1989) "A dihydropyridine carrier system for sustained delivery of 2', 3' dideoxynucleosides to the brain." *J. Med. Chem.* 32, 22–625; Perkins, R. M., Barney, S. Wittrock, R., Clark, P. H., Levin, R. Lambert, D. M., Petteway, S. R., Serafinowska, H. T., Bailey, S. M., Jackson, S., Hamden, M. R. Ashton, R., Sutton, D., Harvey, J. J. and Brown, A. G. (1993) "Activity of BRL47923 and its oral prodrug, SB203657A against a rauscher murine leukemia virus infection in mice." *Antiviral Res.* 20 (Suppl. I). 84; Piantadosi, C., Marasco, C. J., Jr., Norris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) "Synthesis and evaluation of novel ether lipid nucleoside conjugates for anti-HIV-1 activity." *J. Med. Chem.* 34, 1408–1414; Pompon, A., Lefebvre, I., Imbach, J. L., Kahn, S. and Farquhar, D. (1994). "Decomposition pathways of the mono- and bis(pivaloyloxymethyl) esters of azidothymidine-5'-monophosphate in cell extract and in tissue culture medium; an application of the 'on-line ISRP-cleaning HPLC technique." *Antiviral Chem Chemother.* 5, 91–98; Postemark, T. (1974) "Cyclic AMP and cyclic GMP." *Annu. Rev. Pharmacol.* 14, 23–33; Prisbe, E. J., Martin, J. C. M., McGhee, D. P. C., Barker, M. F., Smee, D. F. Duke, A. E., Matthews, T. R. and Verheyden, J. P. J. (1986) "Synthesis and antiherpes virus activity of phosphate an phosphonate derivatives of 9-[(1,3-dihydroxy-2-propoxy)methyl] guanine." *J. Med. Chem.* 29, 671–675; Pucch, F., Gosselin, G., Lefebvre, I., Pompon, a., Aubertin, A. M. Dim, and Imbach, J. L. (1993) "Intracellular delivery of nucleoside monophosphate through a reductase-mediated activation process." *Antiviral Res.* 22, 155–174; Pugaeva, V. P., Klochkeva, S. I., Mashbits, F. D. and Eizengart, R. S. (1969). "Toxicological assessment and health standard ratings for ethylene sulfide in the industrial atmosphere." *Gig. Trf. Prof. Zabol.* 14, 47–48 (*Chem. Abstr.* 72, 212); Robins, R. K. (1984) "The potential of nucleotide analogs as inhibitors of Retro viruses and tumors." *Pharm. Res.* 11 –18; Rosowsky, A., Kim. S. H., Ross and J. Wick, M. M. (1982) "Lipophilic 5'-(alkylphosphate) esters of 1-β-D-arabinofuranosylcytosine and its $N^4$-acyl and 2.2'-anhydro-3'-O-acyl derivatives as potential prodrugs." *J. Med. Chem.* 25, 171–178; Ross, W. (1961) "Increased sensitivity of the walker turnout towards aromatic nitrogen mustards carrying basic side chains following glucose pretreatment." *Biochem. Pharm.* 8, 235–240; Ryu, E. K., Ross, R. J. Matsushita, T., MacCoss, M., Hong, C. I. and West, C. R. (1982). "Phospholipid-nucleoside conjugates. 3. Synthesis and preliminary biological evaluation of 1-β-D-arabinofuranosylcytosine 5' diphosphate [–], 2-diacylglycerols." *J. Med. Chem.* 25, 1322–1329; Saffhill, R. and Hume, W. J. (1986) "The degradation of 5-iododeoxyuridine and 5-bromoethoxyuridine by serum from different sources and its consequences for the use of these compounds for incorporation into DNA." *Chem. Biol. Interact.* 57, 347–355; Saneyoshi, M., Morozumi, M., Kodama, K., Machida, J., Kuninaka, A. and Yoshino, H. (1980) "Synthetic nucleosides and nucleotides. XVI. Synthesis and biological evaluations of a series of 1-β-D-arabinofuranosylcytosine 5'-alky or arylphosphates." *Chem Pharm. Bull.* 28, 2915–2923; Sastry, J. K., Nehete, P. N., Khan, S., Nowak, B. J., Plunkett, W., Arlinghaus, R. B. and Farquhar, D. (1992) "Membrane-permeable dideoxyuridine 5'-monophosphate analogue inhibits human immunodeficiency virus infection." *Mol. Pharmacol.* 41, 441–445; Shaw, J. P., Jones, R. J. Arimilli, M. N., Louie, M. S., Lee, W. A. and Cundy, K. C. (1994) "Oral bioavailability of PMEA from PMEA prodrugs in male Sprague-Dawley rats." *9th Annual AAPS Meeting.* San Diego, Calif. (Abstract). Shuto, S., Ueda, S., Imamura, S., Fukukawa, K. Matsuda, A. and Ueda, T. (1987) "A facile one-step synthesis of 5' phosphatidiylnucleosides by an enzymatic two-phase reaction." *Tetrahedron Lett.* 28, 199–202; Shuto, S. Itoh, H., Ueda, S., Imamura, S., Kukukawa, K., Tsujino, M., Matsuda, A. and Ueda, T. (1988) *Pharm. Bull.* 36, 209–217. An example of a useful phosphate prodrug group is the S-acyl-2-thioethyl group, also referred to as "SATE."

V. Combination Therapy

In other embodiments of the invention, treatment of HDV infection may be accomplished using L-FMAU or other nucleoside or nucleoside analog or organic small molecule meeting the requirements specified herein in combination or alternation with other agents that reduce the level of hepatitis B surface or preS1 antigen in the host, or which are known to otherwise treat hepatitis delta infection, including but not limited to a ribozyme (see U.S. Pat. No. 5,985,621), cytokine including interleukins, interferon (including α, β, or γ), an antibody to hepatitis B surface or preS1 antigen or a transcriptional factor or other mediator of hepatitis B surface or preS1 antigen expression (to impart passive immunity); hepatitis B surface antigen or preS1 antigen or a transcriptional factor or other mediator of hepatitis B surface antigen expression (to impart active immunity), a protein-prenyl transferase inhibitor (Statutory Invention No. HI-345) or peptide hormone (for example, thymosin-alpha-1).

In general, during alternation therapy, an effective dosage of each agent is administered serially, whereas in combination therapy, effective dosages of two or more agents are administered together. The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. The disclosed combination and alternation regiments are useful in the prevention and treatment of HDV infections and other related conditions. In addition, these compounds or formulations can be used prophylactically to prevent or retard the progression of clinical illness in individuals have been exposed to HDV.

VI. Alternative Embodiments for the Treatment of HDV Infection

In an alternative embodiment of the invention, HDV infection can be treated in a host by administering at least one antisense oligonucleotide targeted to the RNA transcript of the hepatitis B surface antigen either alone or in combination with L-FMAU. As used in this disclosure the term "oligonucleotide" encompasses both oligomeric nucleic acid moieties of the type found in nature, such as the deoxyribonucleotide and ribonucleotide structures of DNA and RNA, and man-made analogues that are capable of binding to nucleic acids found in nature. The oligonucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring DNA and RNA structures. Such oligonucleotides may be prepared by methods well-known in the art, for instance using commercially available machines and reagents available from Perkin-Elmer/Applied Biosystems (Foster City, Calif.).

Phosphodiester-linked oligonucleotides are particularly susceptible to the action of nucleases in serum or inside cells, and therefore in a preferred embodiment the oligonucleotides of the present invention are phosphorothioate or methyl phosphonate-linked analogues, which have been shown to be nuclease-resistant. Persons knowledgeable of this field will be able to select other linkages for use in the present invention.

The relative activity of antisense oligonucleotides directed against a specific gene is generally inversely proportional to its location relative to the AUG start codon of the target gene. In the prior art it is known that antisense oligonucleotides targeting sequences more than 60 bases downstream from the AUG start codon of chromosomally integrated HBV surface antigen (HBsAg) gene (S gene) sequences in HBsAg-producing PLC/PRF/5 cells are ineffective in inhibiting HBsAg production, while oligonucleotides placed within 20 bases of the AUG inhibit HBsAg production by 50% to 90%. Therefore, it is preferred that an antisense oligonucleotide targeted the HBV surface antigen gene sequence be chosen such that the oligonucleotide hybridizes within approximately 25 bases of the AUG start codon of the gene. Preferred oligonucleotides directed to the HBV surface antigen gene are described in U.S. Pat. No. 5,646,262 to Korba et al. and include (SEQ ID NO.: 1) CTTAGGACTACACTACAAGAG; (SEQ ID NO.: 2) GACTACACTACAAGAG; (SEQ ID NO.: 3) AGGACTACACTACAAGAGGTA; (SEQ ID NO.: 4) TACACTACAAGAGGTA; (SEQ ID NO.: 5) TCTTCCCCAGGATCCT; (SEQ ID NO.: 6) TTTGGGGCGGACATTG; (SEQ ID NO.: 7) CCTAAGAACAGTTGTT; (SEQ ID NO.: 8) GTACAAGTCGCGTCCCAGG; (SEQ ID NO.: 9) TAGGAGCTCTTCTAAC; (SEQ ID NO.: 10) TATTCCCTAGTCTTGT; (SEQ ID NO.: 11) CAAGAGGTACAAGTC; (SEQ ID NO.: 12) CGACCACCTTTCTAAGACGGG; (SEQ ID NO.: 13) CCTTTCTAAGACGGG; (SEQ ID NO.: 14) TAAGACGGGGTA; (SEQ ID NO.: 15) GACGGGGTACGACAT; (SEQ ID NO.: 16) GTACGACATCTAGAA. Other examples of antisense oligonucleotides for the treatment of HDV infection are disclosed in U.S. Pat. No. 5,985,662 to Isis Pharmaceuticals, Inc. and include: (SEQ ID NO.: 17) CCTGATGTGATGTTCTCCAT; (SEQ ID NO.: 18) GAACTGGAGCCACCAGCAGG; (SEQ ID NO.: 19) GAAAGATTCGTCCCCATGC; and (SEQ ID NO.: 20) CCACTGCATGGCCTGAGGATG.

To select the preferred length for an antisense oligonucleotide, a balance must be struck to gain the most favorable characteristics. Shorter oligonucleotides 10–15 bases in length readily enter cells, but have lower gene specificity. In contrast, longer oligonucleotides of 20–30 bases offer superior gene specificity, but show decreased kinetics of uptake into cells. See Stein et al., PHOSPHOROTHIOATE OLIGODEOXY-NUCLEOTIDE ANALOGUES in "Oligodeoxynucleotides—Antisense Inhibitors of Gene Expression" Cohen, Ed. McMillan Press, London (1988). In a preferred embodiment this invention contemplates using oligonucleotides approximately 14 to 25 nucleotides long.

VII. Synthesis of L-FMAU

The L-nucleosides disclosed herein can be prepared as described in detail below, or by other assays known to those skilled in the art.

Referring to FIG. 3, starting from L-xylose (1a), the key intermediate 1-O-acetyl-2,3,5-tri-O-benzoyl-α-L-ribofuranose (10) was synthesized in a total yield of 20% (L. Vargha, Chem. Ber., 1954, 87, 1351; Holy, A., et al., Synthetic Procedures in Nucleic Acid Chemistry, V1, 163–67). As shown in FIG. 4, compound 10 can also be synthesized from the more expensive starting material L-ribose (Holy, A., et al., Synthetic Procedures in Nucleic Acid Chemistry, V1, 163–67). FIG. 3 illustrates an alternative synthesis of compound 10 (yield of 53%), which was subsequently fluorinated at $C_2$ (J. Org. Chem. 1985, 50, 3644–47) to obtain 1,3,5-tri-O-benzoyl-2-deoxy-2-fluoro-L-arabinofuranose (13), which was condensed with silylated thymine through the bromosugar to provide the protected L-FMAU.

1,2-Di-O-isopropylidene-α-L-xylofuranose (3)

To 650 mL of anhydrous acetone was added 4 mL of conc. sulfuric acid, 5 g of molecular sieve (4A), 80 g of anhydrous cupric sulfate and 50 g of L-xylose and the mixture was stirred at room temperature for 36 hours. The reaction mixture was filtered and washed thoroughly with acetone, the combined filtrate was neutralized with ammonium hydroxide then evaporated to dryness. Ethyl acetate (200 ml) was added, then filtered and evaporated, yielded an oil which was dissolved in 250 ml of 0.2% HCl solution and stirred at room temperature for 2.5 hours. The pH was adjusted to 8 with saturated $NaHCO_3$, then evaporated to dryness, the residue was extracted with ethyl acetate. Removal of the solvent provided a yellow oil of compound 3 (41.7 g, 82.3%).

$^1$H-NMR($CDCl_3$): δ 65.979 (d, J=3.78 Hz,1H, H-1); 4.519 (d, J=3.6 Hz, 1H, H-2); 4.308 (bd, 1H, H-3); 4.080 (m, 3H, H-4 and H-5); 1.321 (s, 3H, $CH_3$); 1.253 (s, 3H, $CH_3$).

1,2-Di-O-isopropylidene-3,5-O-di-(o-tolylsulfonyl)-α-L-xylofuranose (4)

Compound 3 (40 g, 210 mmol) was stirred in 500 ml of anhydrous pyridine at 0° C., while TsCl (75 g, 393 mmol) was dissolved in 100 ml of $CHCl_3$ was added dropwise. After 3 hours, another portion of TsCl (50 g, 262 mmol) in 50 ml of $CHCl_3$ was added the same as above. The mixture was stirred at room temperature for 24 hours, then chilled at 0° C., water (10 mL) was added, then stirred at room temperature for 30 minutes. The reaction mixture was poured into 500 mL of ice-water, extracted with $CHCl_3$ (150 mL×4), washed with 1.5M $H_2SO_4$ (150 mL×4), saturated $NaHCO_3$ (200 mL×2), dried ($MgSO_4$). Removing solvent gave a brown syrup, which upon crystallization from EtOH, gave 4 as a white solid (103.8 g, 99%).

$^1$H-NMR($CDCl_3$): δ 7.282, 7.836 (m, 8H, OTs); 5.849 (d, J=3.51 Hz, 1H, H-1); 4.661, 4.779 (m, 2H, H-3 and H-4); 4.193 (dd, 1H, H-2); 4.011 (d, 2H, H-5); 2.448, 2.478 (2s, 6H, -OTs); 1.261, 1.320 (2s, 6H, $CH_3$).

1,2-Di-O-acetyl-3,5-di-O-p-tolylsulfonylα-β-xylofuranose (5)

Compound 4 (70 g, 140.5 mmol) was dissolved in 700 mL of glacial AcOH and 100 mL of $Ac_2O$ while 50 mL of conc. sulfuric acid was added dropwise at 0° C. The resulting solution was stirred at room temperature overnight and then poured into 1 L of ice-water, extracted with $CHCl_3$ (200 mL×4), washed with saturated $NaHCO_3$, dried ($MgSO_4$). After removing solvent in vacuo, gave 5 as a syrup (84.2 g, crude yield 110%).

Methyl-3,5-di-O-p-tolylsulfonyl-α,β-xylofuranose (6)

The crude 5 (80 g) was stirred in 500 mL of 1% HCl/$CH_3OH$ at room temperature for 30 hours. The solvent was removed under reduced pressure, the residue dissolved in 300 mL of $CHCl_3$, washed with saturated $NaHCO_3$, dried ($MgSO_4$). Removing solvent gave 6 as a syrup (60 g, 90% from 4).

Methyl-2-O-benzoyl-3,5-di-O-p-tolylsulfonyl-α,β-xylofuranoside (7)

The syrup 6 (60 g, 127 mmol) was dissolved in 200 mL of pyridine and stirred at 0° C., while benzoyl chloride (40 mL, 345 mmol) was added dropwise, the resulting solution was stirred at room temperature for 17 hours. It was concentrated to about 50 mL, then poured into 300 mL of ice-water, extracted with $CHCl_3$, washed with $3NH_2SO_4$ and saturated $NaHCO_3$, dried ($MgSO_4$). After evaporation of the solvent, gave 7 as a syrup (71 g, 97%).

Methyl-2,3,5-tri-O-benzoyl-α-β-L-ribofuranoside (9)

The syrup 7 (70 g) and sodium benzoate (100 g, 694 mmol) were suspended in 1200 ml of DMF and mechanically stirred under reflux for 16 hours. It was cooled to room temperature and then poured into 1 L of ice-water, extracted with ether and dried ($MgSO_4$). Evaporation of solvent gave a syrup (50 g, 8a and 8b), which was dissolved in 180 mL of pyridine and benzoylated (BzCl, 20 mL, 172 mmol) for 17 hours at room temperature. After work up, gave 9 as a brown syrup (48 g, 83% from 7).

1-O-acetyl-2,3,5-tri-O-benzoyl-β-L-ribofuranose (10)

Compound 9 (26 g, 54.6 mmol) was treated with 275 mL of glacial acetic acid, 55 ml of acetic anhydride and 16 ml of conc. sulfuric acid at 0° C. to room temperature for 17 hours. Then poured into 1 L of ice-water, extracted with chloroform (200 mL×4). The combined extract was washed with saturated $NaHCO_3$ and dried ($MgSO_4$). Removing solvent gave a brown syrup which was treated with ethanol to give 10 as a white solid (8.8 g, 32%).

m.p.124.7° C., lit.129°–130° C.; D from: 130°–131° C. $[\alpha]_D$=−45.613 (C 1.0, $CHCl_3$), D form: $[\alpha]_D$=+44.2. $^1$H-NMR($CDCl_3$): δ 7.317, 8.134 (m, 15H, OBz); 6.437 (s, 1H, H-1); 5.835 (m, 2H, H-2 and H-3); 4.649 (m, 3H, H-4 and H-5); 2.003 (s, 3H, $CH_3$ COO—).

1-O-acetyl-2,3,5-tri-O-benzoyl-β-L-ribofuranose (from L-ribose)

L-Ribose (5 g, 33.3 mmol) was suspended in 120 mL of 1% HCl/MeOH and stirred at room temperature for 3 hours, when a clear solution was obtained. The reaction was quenched by adding 30 mL of anhydrous pyridine, then evaporated under reduced pressure. The resulting syrup was coevaporated with pyridine (30 ml×2), then dissolved in 80 ml of anhydrous pyridine, and stirred at 0° C. while benzoyl chloride (20 ml, 172 mmol) was added dropwise. After stirring at room temperature for 17 hours, the reaction was complete. Water (10 mL) was added and the mixture was stirred at room temperature for 0.5 hours, then concentrated to about 50 mL, poured into 150 mL of ice-water, extracted with chloroform (50 ml×4), washed successively with $3NH_2SO_4$ (30 mL×2), saturated $NaHCO_3$ (30 mL×3), dried ($MgSO_4$). Removing solvent gave 9 as a syrup of 13 g.

The crude 9 was dissolved in 80 mL of HBr/AcOH (45%, w/v) and stirred at room temperature for 1.5 hours. To this mixture, was added glacial acetic acid (50 mL) and the resulting solution stirred at 0° C., while 34 mL of water was added slowly to keep the temperature below 7° C., then it was stirred at room temperature for 1 hour, poured into 200 mL of ice-water, extracted with chloroform (50 mL×5), the combined extracts were washed with saturated $NaHCO_3$, dried ($MgSO_4$). Removing solvent gave a syrup (13 g), which was dissolved in 40 mL of anhydrous pyridine, stirred at 0° C., when acetic anhydride (14 mL, 148.4 mmol) was added dropwise. After the reaction completed, it was poured into 150 mL of ice-water, extracted with chloroform (50 mL×4), washed successively with $3NH_2SO_4$ (30 mL×2), saturated $NaHCO_3$ (50 mL×2), dried ($MgSO_4$). Removing solvent and treating with methanol, gave a white solid (9.2 g, 53.7% from L-ribose).

1,3,5-Tri-O-benzoyl-α-L-ribofuranose (11)

Compound 10 (9 g, 17.84 mmol) was stirred in 100 mL of $CH_2Cl_2$ at 0° C. while 70 mL of $CH_2Cl_2$ containing HBr (3.2 g, 30.5 mmol) was added in one portion. The mixture was stirred at 0° C. for 3.5 hrs, water (55 ml) was added and the mixture stirred at room temperature for 18 hours. The organic layer was separated, washed with saturated $NaHCO_3$, dried ($MgSO_4$). After evaporation of the solvent, a foam was obtained, which upon recrystallization from $CH_2Cl_2$ and n-hexane, gave 11 as a white solid (6.2 g, 75.5%).

m.p. 137°–138° C., lit. 140°–141° C., $[\alpha]_D$=−81.960 (C 0.55, $CHCl_3$; D form: $[\alpha]_D$=+83.71. $^1$H-NMR($CDCl_3$): δ 7.312, 8.187 (m, 15H, OBz); 6.691 (d, J=4.59 Hz, H-1); 5.593 (dd, $J_{4-3}$=6.66 Hz; $J_{2-3}$=1.8 Hz, 1H, H-30; 4.637, 4.796 (m, 4H, H-2, H-4 and H-5); 2.3 (b, OH).

1,3,5-Tri-O-benzoyl-2-O-imidazosulfuryl-α-L-ribofuranose (12)

Compound 11 (5.94 g, 12.84 mmol) was stirred in 50 mL of anhydrous $CH_2Cl_2$ at −15° C. (dry ice-$CCl_4$). Anhydrous DMF (15 mL) and sulfuryl chloride (3.2 mL, 3.98 mmol) was added sequentially. The solution was stirred at −15° C. for 30 minutes then left at room temperature for 4 hours. Imidazole (8.7 g, 12.78 mmol) was added in three portions while the reaction mixture was cooled in an ice bath, then it was stirred at room temperature for 17 hours. The mixture was poured into 150 mL of ice-water and the water phase extracted with $CH_2Cl_2$ (50 mL×3). The combined organic layer was washed with water, dried ($MgSO_4$).

After purification on column (Hexane: EtOAc/5:1–1:1) gave 12 as a white solid (3.7 g, 49%).

m.p. 124.5°–125.5° C., lit: 129° C.; $[\alpha]_D$=−68.976; D form: +66.154. $^1$H-NMR ($CDCl_3$): δ 6.9, 8.2 (m, 18H, Ar—H); 6.67 (d, J=4.4 Hz, 1H, H-1); 5.59 (dd, 1H, H-3), 5.21 (dd, 1H, H-2); 4.5, 4.8 (m, 3H, H-4 and H-5).

1,3,5-Tri-O-benzoyl-2-deoxy-2-fluoro-α-L-arabinofuranose (13)

A suspension of 12 (3.33 g, 5.62 mmol), $KHF_2$ (1.76 g, 22.56 mmol) in 30 mL of 2,3-butanediol was stirred under argon. It was heated to 150° C. while 1 mL of $HF/H_2O$ (48%, 27.6 mmol) was added and the mixture was stirred at 160° C. for 1.5 hours. Brine-ice was added to quench the reaction, then extracted with methylene chloride (50 mL×4), the combined extract was washed with brine, water, saturated $NaHCO_3$, dried over anhydrous magnesium sulfate and activated carbon (Darco-60). It was poured on a silica gel pad (5 cm×5 cm), washed with methylene chloride and then EtOAc, to give a syrup which from 95% EtOH, 13 (1.3 g, 49.8%) was crystallized.

m.p. 77°–78° C.; lit.: 82° C. $^1$H-NMR($CDCl_3$): δ 7.314, 8.146 (m, 15H, OBz); 6.757 (d, J=9.1 Hz, 1H, H-1); 5.38 (d, J=48.5 Hz, 1H, H-2); 5.630 (dd, J=22.5Hz, 1H, H-3); 4.768 (m, 3H, H-4 and H-5).

Compound 13 (464 mg, 1 mmol) was dissolved in 10 mL of methylene chloride while 1.4 mL of HBr/AcOH (45% w/v) was added. The solution was stirred at room temperature for 24 hours, then evaporated to dryness, the residue was dissolved in 20 mL of methylene chloride, washed with water, saturated $NaHCO_3$, dried ($MgSO_4$). Filtration and evaporation gave the bromosugar 14 (100%, based on TLC).

$N^1$-(2'-Deoxy-2'-fluoro-3',5'-di-O-benzyl-β-L-arabinofuranosyl)-thymine (17)

To a solution of 13 (400 mg, 0.86 mmol) in anhydrous $CH_2Cl_2$ (10 mL) was added hydrogen bromide in acetic acid (45% w/v, 1.5 mL), and the resulting solution was stirred at room temperature for 17 hours. After evaporation of the solvent and coevaporation with toluene, 14 was obtained.

At the same time, thymine (215 mg, 1.72 mmol) was refluxed in HMDS (25 ml) under nitrogen for 17 hours to get a homogeneous solution. After evaporation of the solvent, gave a silylated thymine.

A solution of 14 in dichloroethane (50 mL) was added to the silylated thymine and the resulting solution was refluxed under nitrogen for 3 days. Water was added and then extracted with $CHCl_3$. The organic layer was washed with water, brine and dried ($MgSO_4$). Evaporation of the solvent gave the crude product, which was purified on preparative TLC using 2% $MeOH/CHCl_3$ to give 17 (235 mg, 58%).

m.p. 99°–101° C. UV(Methanol): 230, 264 nm $[\alpha]_D$=+22.397. $^1$H-NMR ($CDCl_3$): δ 7.343–8.389 (m, 12H, Ar—H, NH); 6.34 (dd, $J_{H-H}$=2.97 Hz, $J_{F-H}$=28.32 Hz, 1H, H-1'); 5.383 (dd, $J_{H-H}$=2.7 Hz, $J_{F-H}$=63.27 Hz, 1H, H-2'); 5.565 (dd, 1H, H-3'); 4.812 (d, 2H, H-5'); 4.466 (m, 1H, H-4'); 1.775 (s, 3H, $CH_3$) Anal. ($C_{24}H_{21}N_2O_7F$), C: 61.01; H, 4.57; N: 5.73; F: 3.92.

$N^1$-(2'-Deoxy-2'-fluoro-β-L-arabinofuranosyl)-thymine (18)

Compound 17 (145 mg, 0.309 mmol) was treated with $NH_3/CH_3OH$ at room temperature for 18 hours. After evaporation of the solvent and purified on preparative TLC (15% $MeOH/CHCl_3$, 18 (70 mg, 87.5%) was obtained.

m.p. 174°–175° C. UV: 264 nm, $[\alpha]_D$=−104.36. $^1$H-NMR (DMSO-$d_6$): δ 11.401 (s, 1H, NH); 7.575 (s, 1H, H-6); 6.093 (dd, $J_{H-H}$=4.41 Hz, $J_{F-H}$=15.6 Hz, H-1'); 5.844 (d, 1H, 3'-OH); 5.019 (dt, $J_{F-H}$=53.3 Hz, 1H, H-2'); 5.087 (t, 1H, 5'-OH); 4.194 (dq, 1H, H-3'); 3.647 (m, 3H, H-4' and H-5'); 1.781 (s, 3H, $CH_3$). Anal. ($C_{10}H_{13}N_2FO_5$), C: 44.80; H: 4.97; N: 10.04; F: 7.03.

5'-alkyl and Mono, -di- and tri-phosphate Derivatives of L-FMAU

The derivative of L-FMAU wherein there is an alkyl group in the 5'-position can be prepared via protection of the thymine base using sodium hydride and t-butyl-di-phenyl silo protecting group. Benzoylation of the 5'-hydroxyl group can be achieved with benzoyl hydride. The resulting compound can be desilylated using tetrabutylammonium fluoride. Introduction of alkyl groups to the 5'-position is accomplished using sodium hydride and alkyl bromide, the benzoyl group can be removed with a base.

The mono, di and triphosphate derivative of L-FMAU can be prepared as described below. The monophosphate can be prepared according to the procedure of Imai et al., *J. Org. Chem.*, 34(6), 1547–1550 (June 1969). For example, about 100 mg of L-FMAU and about 280 μL of phosphoryl chloride are reacted with stirring in about 8 mL of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluent gives ammonium L-FMAU-5'-monophosphate.

The diphosphate can be prepared according to the procedure of Davisson et al., *J. Org. Chem.*, 52(9), 1794–1801 (1987). L-FMAU diphosphate can be prepared from the corresponding tosylate, that can be prepared, for example, by reacting the nucleoside with tosyl chloride in pyridine at room temperature for about 24 hours, working up the product in the usual manner (e.g., by washing, drying, and crystallizing it).

The triphosphate can be prepared according to the procedure of Hoard et al., *J. Am. Chem. Soc.*, 87(8), 1785–1788 (1965). For L-FMAU is activated (by making a imidazolide, according to methods known to those skilled in the art) and treating with tributylammonium pyrophosphate in DMF. The reaction gives primarily the triphosphate of the nucleoside, with some unreacted monophosphate and some diphosphate. Purification by anion exchange chromatography of a DEAE column is followed by isolation of the triphosphate, e.g., as the tetrasodium salt.

VIII. Illustrative Example

The woodchuck was used as an experimental model of chronic HDV infection to assess the effect of L-FMAU treatment on HDV replication. Woodchucks chronically infected with WHV were infected with a woodchuck-adapted HDV inoculum derived from a laboratory infectious clone. Nine of eleven infected animals were determined to have chronic HDV infection, as defined by RT/PCR-detectable HDV viremia (Niro et al. (1997) *Hepatology* 25, 728–734) for at least 74% of bleed dates for at least 11 months prior to the initiation of treatment. The range of duration of viremia prior to the start of the study was 11.4–20 months; the range of positive bleed dates was 74% to 100%. Animals in the treatment group (4) were given 10 mg/kg L-FMAU daily; animals in the control group (5) were given placebo. Serum samples were obtained before the initiation of treatment, and at weeks 2, 4, 8, 12, 16 and 20. Serum samples were analyzed for WHV DNA, WHV surface antigen and HDV RNA.

Figure 6A:
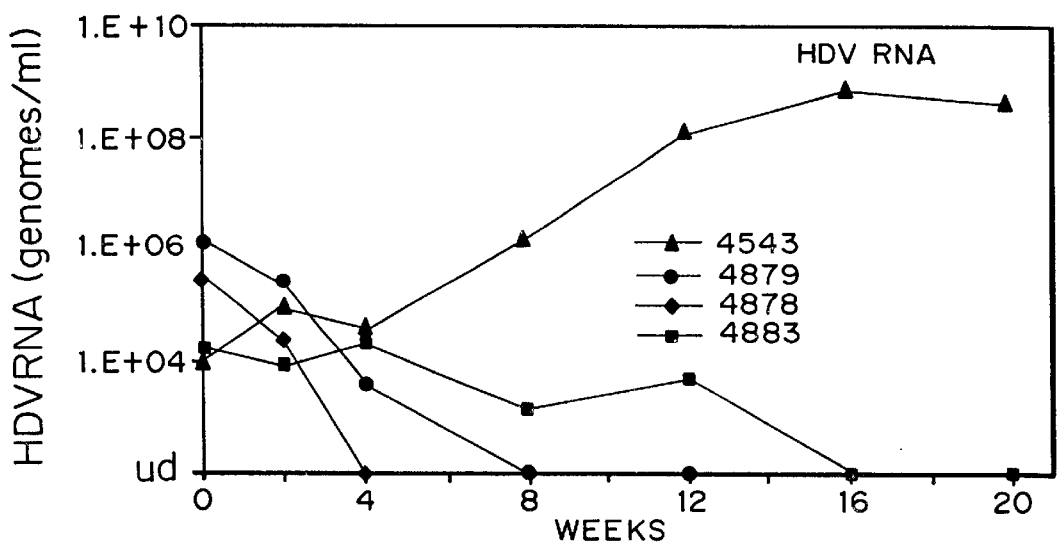
FIG. 6A is a line graph of weeks of treatment of L-FMAU in woodchucks versus genomic equivalents per ml of HDV RNA in serum and demonstrates the decrease in HDV RNA in HDV-infected woodchucks treated with L-FMAU over twenty weeks. Woodchucks chronically infected with WHV were infected with a woodchuck-adapted HDV inoculum derived from a laboratory infectious clone. Chronicity was established by detectable HDV viremia for at least 74% of bleed dates for at least 11 months prior to the initiation of treatment. The results indicate that treatment with L-FMAU causes a significant decrease in serum HDV-RNA.
Figure 6B:
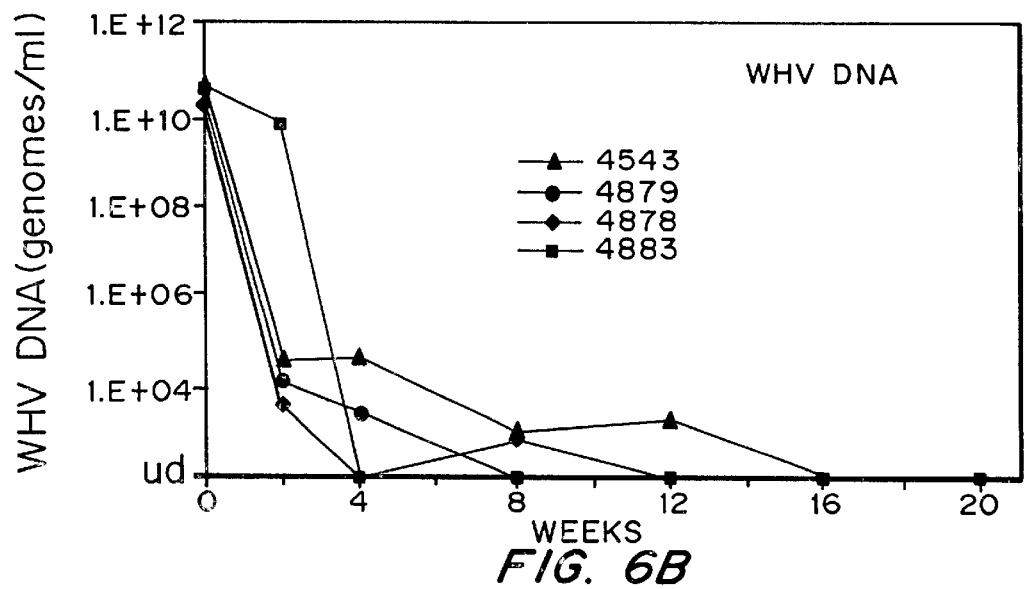
FIG. 6B is a line graph of weeks of treatment of L-FMAU in woodchucks versus woodchuck serum WHV-DNA in genomic equivalents per ml. Woodchucks chronically infected with WHV were infected with a woodchuck-adapted HDV inoculum derived from a laboratory infectious clone. Chronicity was established by detectable HDV viremia for at least 74% of bleed dates for at least 11 months prior to the initiation of treatment. The results indicate that treatment with L-FMAU causes a significant decrease in serum WHV-DNA.
Figure 6C:
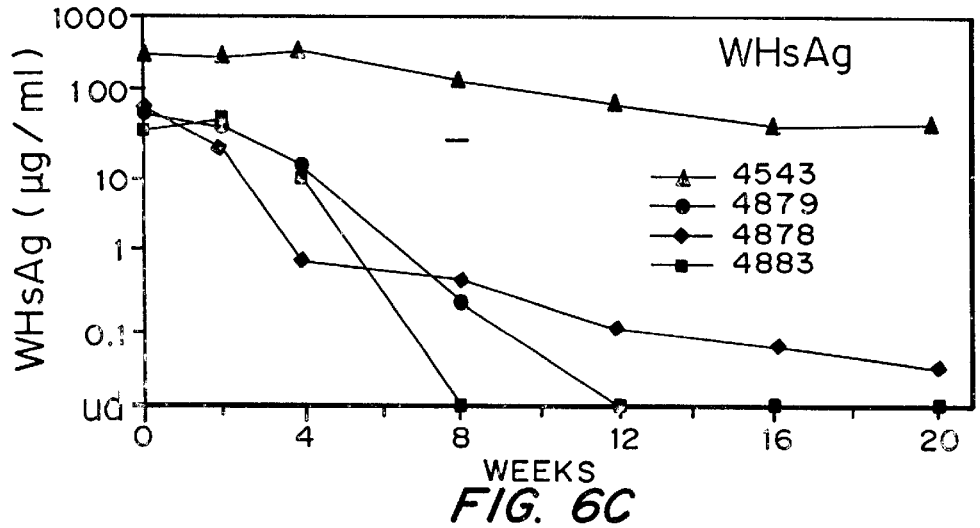
FIG. 6C is a line graph of weeks of treatment of L-FMAU in woodchucks versus woodchuck serum WHsAg in μg/mL. Woodchucks chronically infected with WHV were infected with a woodchuck-adapted HDV inoculum derived from a laboratory infectious clone. Chronicity was established by detectable HDV viremia for at least 74% of bleed dates for at least 11 months prior to the initiation of treatment. The results indicate that treatment with L-FMAU causes a significant decrease in serum WHsAg.
Figure 7A:
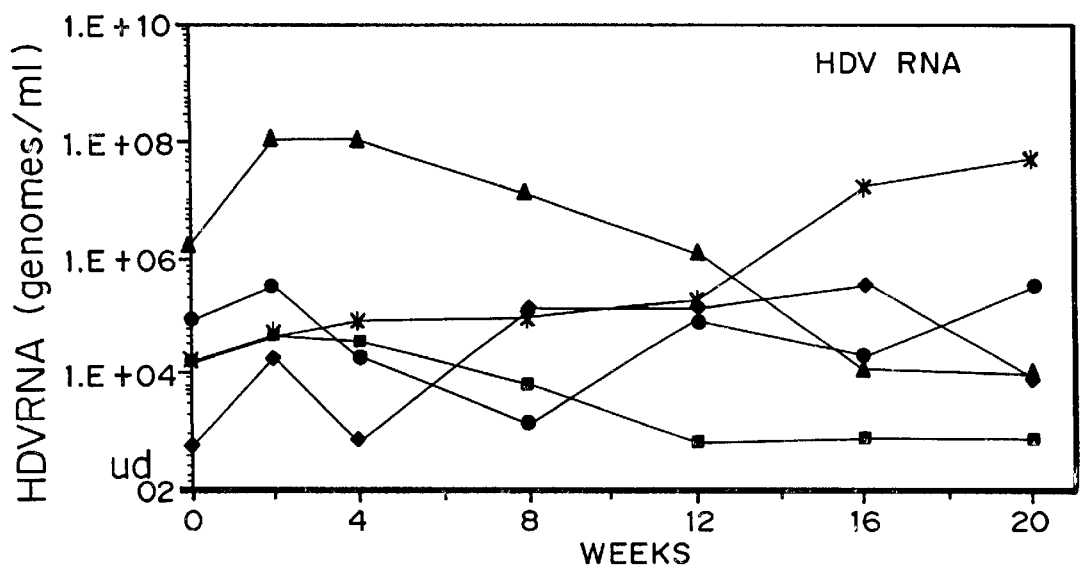
FIG. 7A is a line graph showing the presence of HDV RNA in the serum of HDV-infected woodchucks over twenty weeks in the absence of L-FMAU.
Figure 7B:
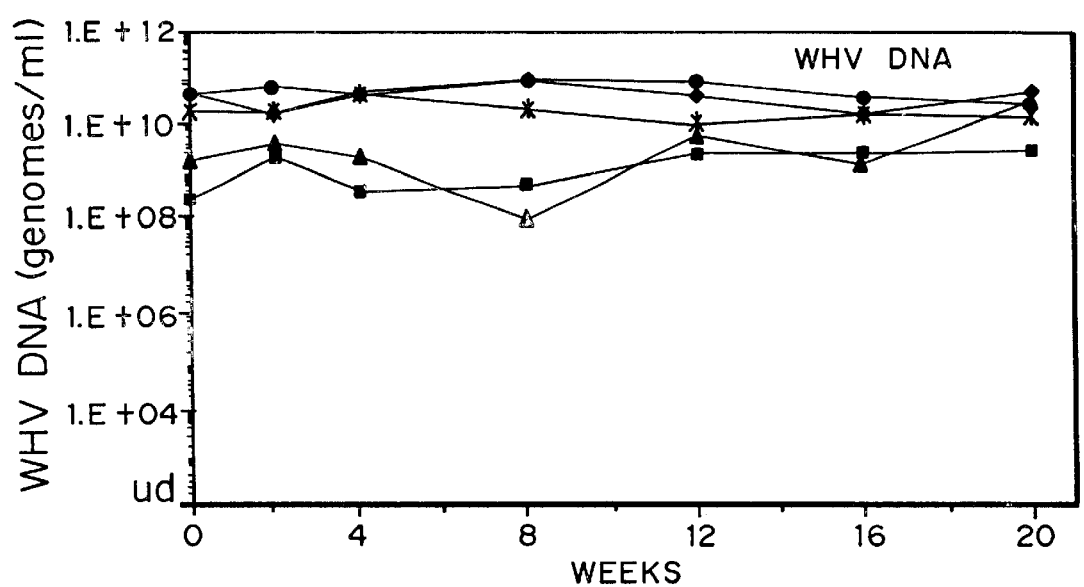
FIG. 7B is a line graph showing serum levels of WHV-DNA in woodchucks over twenty weeks in the absence of L-FMAU.
Figure 7C:
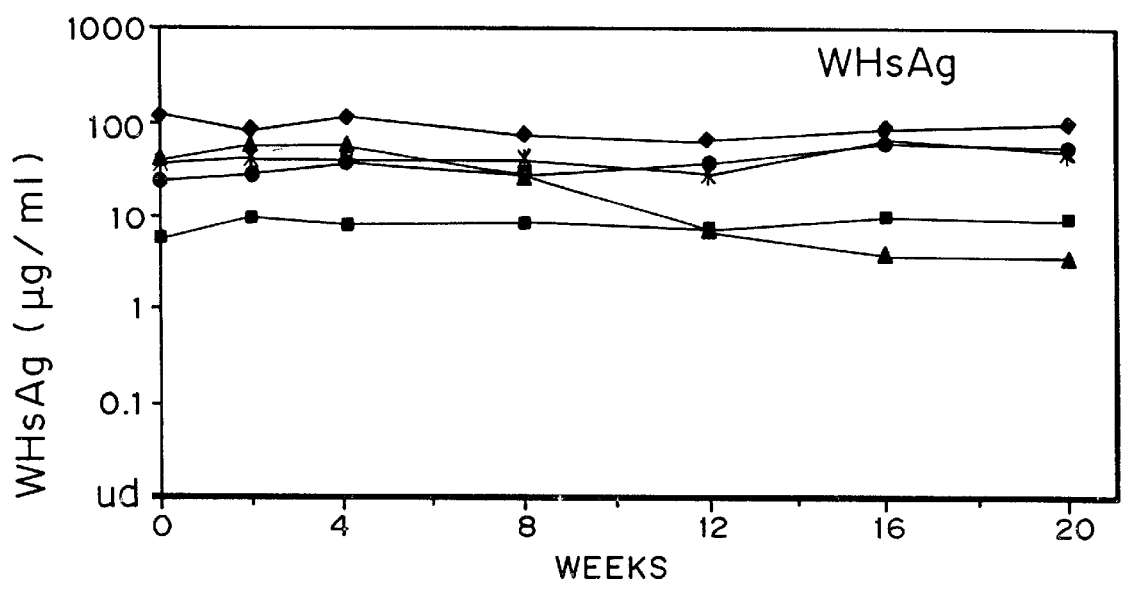
FIG. 7C is a line graph showing serum levels of WHsAg in woodchucks over twenty weeks in the absence of L-FMAU.

All treated animals exhibited marked decreases in serum WHV DNA by 4 weeks of treatment (>$10^7$-fold reduction), as has been previously observed with this compound (Peek, S. et al. (2001) *Hepatology* 33, 254–66) (FIG. 6B). A nearly 1,000-fold decrease in surface antigen levels was observed by 12 weeks in all but one (animal 4543) of the treated animals (FIG. 6C). HDV RNA became undetectable in 3/4 treated animals by 16 weeks of treatment (FIG. 6A). No substantial changes were observed for any of these viral markers in the control group (FIG. 7A, FIG. 7B, FIG. 7C, FIG. 8).

Notably, decreased HDV viremia correlated with decreased serum levels of surface antigen. HDV virema became undetectable following reduction of hepatitis B surface antigen concentrations by 100-fold or more and notably, after reduction to less than 1 microgram/mL. This effect was sustained for the remainder of the treatment period. HDV RNA became undetectable in all animals exhibiting decreased levels of surface antigen. One animal in the treated group, animal 4543, did not exhibit decreased levels of surface antigen (although WHV DNA levels did decrease), and HDV viremia remained high in this animal.

Figure 8:
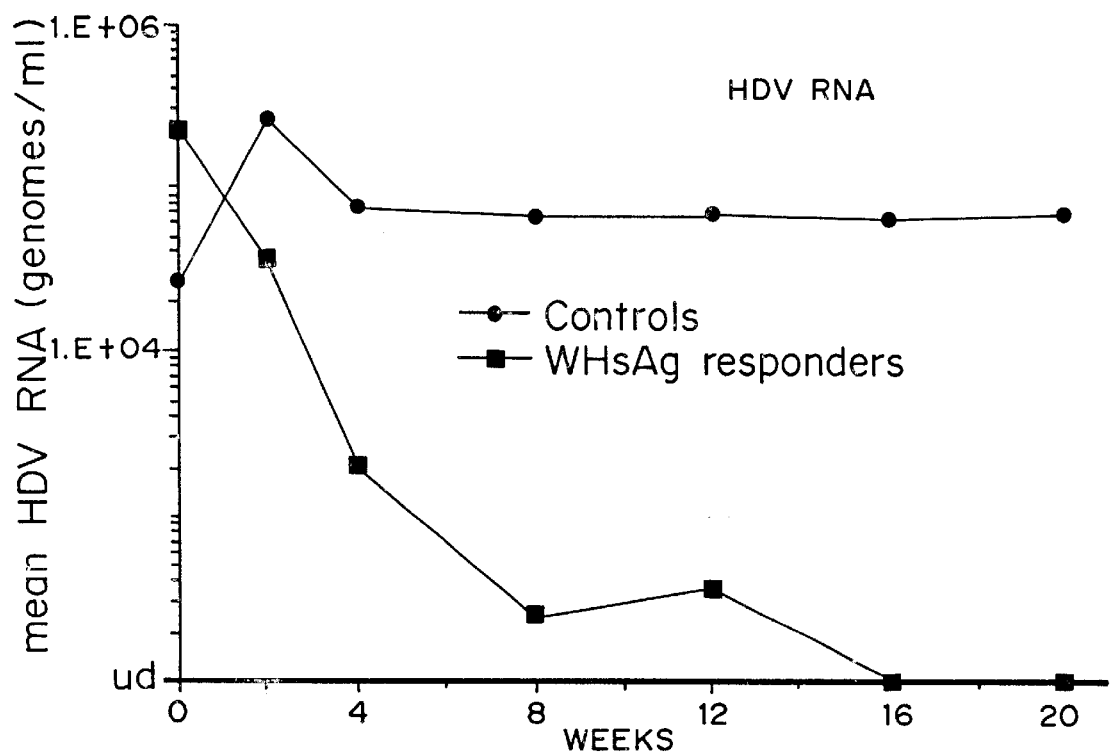
FIG. 8 is a line graph of mean serum HDV RNA in genomic equivalents per ml versus weeks. The graph compares the mean serum HDV level in the five untreated woodchucks (circle data points) with that of the L-FMAU treated woodchucks 4878, 4879, and 4883 (square data points), in which WHsAg levels dropped more than 100-fold during treatment (see FIG. 6B). The graph shows a dramatic decline in HDV RNA in these three treated animals by 8 weeks of the treatment compared with the level in these same animals at the start of treatment and compared with levels in the five untreated animals at any time.

When the three L-FMAU- treated animals in which WHsAg declined are grouped together (WHsAg-responders), it is clear that HDV RNA levels decline dramatically compared to pre-treatment levels and compared with levels in the control group at any time (FIG. 8). Statistical analysis by Student's t-test indicates this dramatic decline is highly statistically significant (P=0.02 for paired, 1-tail comparison of week 0 vs. week 20 in the WHsAg-responders, and P=0.02 for unpaired 1-tail comparison of week 20 levels in untreated vs WHsAg-responders).

It was discovered that L-FMAU is a potent inhibitor of HDV in chronically infected animals, in part due to its strong suppression of surface antigen expression. Previous studies have shown a close correlation between levels of chronic HDV viremia and disease severity (Smedile, A. et al. (1986) *Hepatology* 6, 1297–302; Smedile, A. et al. (1987) *Prog Clin Biol Res* 234, 235–41; Niro, G. A. et al. (1997) *Hepatology* 25, 728–734; Shakil, A. O. et al. (1997) *Virology* 234, 160–7). Because there is no long-standing cellular repository for HDV as there is for HBV (i.e., no covalently closed circular DNA), and the half-life of HDV-infected cells may be as short as two weeks (Netter, H. J. et al. (1993) *J Virol* 67, 3357–62.), based on these results, L-FMAU and other nucleosides, nonnucleosides, and nucleoside analogs could be used to eliminate HDV infection altogether in treated patients by prolonged reduction of viremia to low levels.

IX. Preparation of Pharmaceutical Compositions

Humans suffering from diseases caused by HDV infection can be treated by administering to the patient an effective amount of a nucleoside or nucleoside analog or a pharmaceutically acceptable salt or prodrug thereof, in the presence of a pharmaceutically acceptable carrier or diluent, that reduces the level of hepatitis B surface or preS1 antigen in the host to not more than approximately 100-fold or more, and preferably, 200- or 500-fold relative to pretreatment values in vivo or in vitro, or with respect to HBsAg, to not more than 1, and preferably, 0.5 or 0.1 microgram per milliliter in vivo, as measured in serum or plasma using standard immunoassays. In a preferred embodiment, the nucleoside is 2'-fluoro-5-methyl-β-L-arabinofuranosyl-uridine or a pharmaceutically acceptable prodrug or salt thereof. The active compound (or prodrug form thereof) can be administered by any appropriate route, for example, orally, parenterally, intravenously, intradermally, subcutaneously, or topically, in liquid or solid form.

The active compound (or prodrug thereof) is included in the pharmaceutically acceptable carrier or diluent in an amount sufficient to deliver to a patient a therapeutically effective amount of compound to reduce HDV viremia or the symptoms thereof in vivo without causing serious toxic effects in the patient treated. A "reducing amount" is meant as an amount of active ingredient sufficient to decrease levels of HDV viremia as measured by, for example, an assay such as the ones described herein or other known methods.

A preferred dose of the compound for all of the above-mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using weight of the derivative, or by other means known to those skilled in the art.

The compound is conveniently administered in units of any suitable dosage form, including but not limited to one containing 7 to 3000 mg, preferably 70 to 1400 mg of active ingredient per unit dosage form. An oral dosage of 50–1000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors. The compound or a pharmaceutically acceptable derivative or salts thereof can also be mixed with other active materials that do not impair the desired action, or with materials that supplement the desired action, such as antibiotics, antifungals, anti-inflammatories, or other anti-virals, including nucleoside anti-HIV compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of the appended claims.

What is claimed is:

1. A method for the treatment of hepatitis delta infection comprising administering to a host an effective amount of a β-L nucleoside of the formula

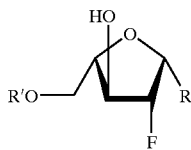

wherein R is 5-methyl uracil (also referred to as thymine) and R' is hydrogen, acyl, alkyl, monophosphate, diphosphate, triphosphate, or a phosphate prodrug or a pharmaceutically acceptable salt thereof.

2. The method of claim 1, wherein the compound is 2'-fluoro-5-methyl-β-L-arabinofuranosyl-uridine.

3. The method of claim 2, wherein the compound is a pharmaceutically acceptable salt of 2'-fluoro-5-methyl-β-L-arabinofuranosyl-uridine.

4. The method of claim 2, wherein the compound is a prodrug of 2'-fluoro-5-methyl-β-L-arabinofuranosyl-uridine.

5. The method of claim 2, wherein the compound is administered in an enantiomerically enriched form.

6. The method of claim 1, wherein the compound is at least 95% in its designated enantiomeric.

7. The method of claim 1, wherein the compound is administered in a pharmaceutically acceptable carrier.

8. The method of claim 2, wherein the pharmaceutically acceptable carrier is suitable for oral delivery.

9. The method of claim 7, wherein the pharmaceutically acceptable carrier is suitable for intravenous delivery.

10. The method of claim 7, wherein the pharmaceutically acceptable carrier is suitable for parenteral delivery.

11. The method of claim 8, wherein the pharmaceutically acceptable carrier is suitable for intradermal delivery.

12. The method of claim 7, wherein the pharmaceutically acceptable carrier is suitable for subcutaneous delivery.

13. The method of claim 7, wherein the pharmaceutically acceptable carrier is suitable for topical delivery.

14. The method of claim 7, wherein the compound is in the form of a dosage unit.

15. The method of claim 7, wherein the dosage unit contains 10 to 1500 mg of the compound.

16. The method of claim 14 or 15, wherein the dosage unit is a tablet or capsule.

* * * * *

SEQUENCE LISTING

```
<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 1
cttaggacta cactacaaga g                                             21

<210> SEQ ID NO 2
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 2
gactacacta caagag                                                   16

<210> SEQ ID NO 3
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 3
aggactacac tacaagaggt a                                             21

<210> SEQ ID NO 4
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 4
tacactacaa gaggta                                                   16

<210> SEQ ID NO 5
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 5
tcttccccag gatcct                                                   16
```

<210> SEQ ID NO 6
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 6 tttgggcgg acattg                                                      16

<210> SEQ ID NO 7
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 7
cctaagaaca gttgtt                                                     16

<210> SEQ ID NO 8
<211> LENGTH: 19
<212> TYPE: DNA
<213> ORGANISM: Artificial Sequence
<220> FEATURE:
<223> OTHER INFORMATION: antisense oligonucleotide

<400> SEQUENCE: 8
gtacaagtcg cgtcccagg                                                  19

<210> SEQ ID NO 9
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 9
taggagctct tctaac                                                     16

<210> SEQ ID NO 10
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 10
tattccctag tcttgt                                                     16

<210> SEQ ID NO 11
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 11
caagaggtac aagtc                                                      15

<210> SEQ ID NO 12
<211> LENGTH: 21
<212> TYPE: DNA
<213> ORGANISM: Artificial Sequence
<220> FEATURE:

-continued

<223> OTHER INFORMATION: antisense oligonucleotide

<400> SEQUENCE: 12
cgaccacctt tctaagacgg g                                    21

<210> SEQ ID NO 13
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 13
cctttctaag acggg                                           15

<210> SEQ ID NO 14
<211> LENGTH: 12
<212> TYPE: DNA
<213> ORGANISM: Artificial Sequence
<220> FEATURE:
<223> OTHER INFORMATION: antisense oligonucleotide

<400> SEQUENCE: 14
taagacgggg ta                                              12

<210> SEQ ID NO 15
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 15
gacggggtac gacat                                           15

<210> SEQ ID NO 16
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 16
gtacgacatc tagaa                                           15

<210> SEQ ID NO 17
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 17
cctgatgtga tgttctccat                                      20

<210> SEQ ID NO 18
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 18
gaactggagc caccagcagg                                      20

```
-continued

<210> SEQ ID NO 19
<211> LENGTH: 19
<212> TYPE: DNA
<213> ORGANISM: Artificial Sequence
<220> FEATURE:
<223> OTHER INFORMATION: antisense oligonucleotide

<400> SEQUENCE: 19
gaaagattcg tccccatgc                                              19

<210> SEQ ID NO 20
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 20
ccactgcatg gcctgaggat g                                           21
```